(12) United States Patent
Petroff, II et al.

(10) Patent No.: US 10,221,153 B2
(45) Date of Patent: Mar. 5, 2019

(54) DIBENZOTHIOPHENE COMPOUNDS

(71) Applicant: Saint Louis University, St. Louis, MO (US)

(72) Inventors: John T. Petroff, II, St. Louis, MO (US); Ryan D. McCulla, St. Louis, MO (US); Christopher Arnatt, Manchester, MO (US)

(73) Assignee: Saint Louis University, St. Louis, MO (US)

( * ) Notice: Subject to any disclaimer, the term of this patent is extended or adjusted under 35 U.S.C. 154(b) by 0 days.

(21) Appl. No.: 15/970,584

(22) Filed: May 3, 2018

(65) Prior Publication Data

US 2018/0319765 A1    Nov. 8, 2018

Related U.S. Application Data

(60) Provisional application No. 62/574,431, filed on Oct. 19, 2017, provisional application No. 62/500,909, filed on May 3, 2017.

(51) Int. Cl.

| | | |
|---|---|---|
| *C07D 333/76* | (2006.01) | |
| *H01L 51/00* | (2006.01) | |
| *H01L 51/52* | (2006.01) | |
| *H01L 51/50* | (2006.01) | |
| *H01L 51/56* | (2006.01) | |

(52) U.S. Cl.
CPC ........ *C07D 333/76* (2013.01); *H01L 51/0074* (2013.01); *H01L 51/5012* (2013.01); *H01L 51/5206* (2013.01); *H01L 51/5221* (2013.01); *H01L 51/56* (2013.01)

(58) Field of Classification Search
CPC .................................................. C07D 333/76
USPC ......................................................... 549/44
See application file for complete search history.

(56) References Cited

U.S. PATENT DOCUMENTS

| | | | |
|---|---|---|---|
| 4,965,284 A | 10/1990 | Nair et al. | |
| 9,123,903 B2 | 9/2015 | Lin et al. | |
| 9,475,889 B2 | 10/2016 | Shukla | |
| 9,587,172 B2 | 3/2017 | Lee et al. | |
| 9,590,184 B2 | 3/2017 | Lee et al. | |
| 9,590,185 B2 | 3/2017 | Cho et al. | |

FOREIGN PATENT DOCUMENTS

| | | |
|---|---|---|
| WO | 2009085344 A2 | 7/2009 |
| WO | 2012101926 A1 | 8/2012 |
| WO | 2015140073 A1 | 9/2015 |
| WO | 2016097983 A1 | 6/2016 |

OTHER PUBLICATIONS

Barder, T.E., et al., "Catalysts for Suzuki-Miyaura Coupling Processes: Scope and Studies of the Effect of Ligand Structure," 2005, JACS, 127/13:4685-4696, Abstract Only, 2 pages.
Bourdillon, M.T., et al., "Oxidation of Plasmalogen, Low-Density Lipoprotein, and RAW 264.7 Cells by Photoactivatable Atomic Oxygen Precursors," 2014, Photochem Photobiol, 90/2:386-393, 18 pages.
Cai, X. et al., "Electron and Hole Transport in a Wide Bandgap Organic Phosphine Oxide for Blue Electrophosphorescence," 2008, Applied Physics Letters, 92:083308, 3 pages.
Grimsdale, A.C., et al., "Synthesis of Light-Emitting Conjugated Polymers for Applications in Electroluminescent Devices," 2009, Chem Rev, 109/3:897-1091, Abstract Only, 3 pages.
Huang, T-H., et al., "Materials for High Performance Single-Layer OLED Devices," 2006, Advanced Materials, 18:602-606, 4 pages.
Kim, H.J., et al., "Synthesis and Characterization of New Dibenzothiophene-based Host Materials for Blue Phosphorescent Organic Light-Emitting Diodes," Molecular Crystals and Liquid Crystals, 621/1, downloaded Jan. 13, 2017, http://www.tandfonline.com/doi/abs/10.1080/15421406.2015.1085835?src=recsys&jounal, 5 pages.
Korang, J., et al., "Photoinduced DNA Cleavage by Atomic Oxygen Precursors in Aqueous Solutions," 2013, RSC Advances, 3:12390-12397, Abstract Only, 5 pages.
Miller, S. C., "Profiling Sulfonate Ester Stability: Identification of Complementary Protecting Groups for Sulfonates," 2010, J Org Chem, 75/13:4632-4635, 9 pages.
Moss, K.C., et al., "Tuning the Intramolecular Charge Transfer Emission from Deep Blue to Green in Ambipolar Systems Based on Dibenzothiophene S,S-Dioxide by Manipulation of Conjugation and Strength of the Electron Donor Units," 2010, JOC, 75/20:6771-6781, Abstract Only, 2 pages.
Na, Y.J., et al., "Synthesis of Dibenzothiophene-Based Host Materials with a Dimesitylborane Substituent and Their Green PHOLED Performances," 2015, Dalton Trans, 44/18:8360-8363, Abstract Only, 1 page.
Na, Y.J., et al., "Synthesis of Dibenzothiophene-Based Host Materials and Their Blue Phosphorescent Device Performances," 2015, Organic Electronics, 22:92-97, Abstract Only, 3 pages.
Nag, M., et al., "Photochemistry and Photophysics of Halogen-Substituted Dibenzothiophene Oxides1," 2004, JOC, 69/24:8177-8182, 6 pages.
Pahlavanlu, P., et al., "Controlled Intramolecular Charge Transfer using a Sulfur-Containing Acceptor Group," 2016, J Phys Chem C, 120/1:70-77, Abstract Only, 2 pages.
Petroff, II, J.T., et al., "Synthesis of Asymmetrical Dienzothiophene Sulfonate Esters," 2016, Tetrahedron Letters, 57/42:4723-4726, 4 pages.
Tlach, B.C., et al., "Tuning the Optical and Electronic Properties of 4,8-Disubstituted Benzobisoxazoles via Alkyne Substitution," 2011, J Org Chem, 76/21:8670-8681, Abstract Only, 2 pages.
Wauchope, O.R., et al., "Photocleavage of Plasmid DNA by Dibenzothiophene S-oxide Under Anaerobic Conditions," 2007, J Sulfur Chem, 28/1:11-16, 6 pages.
J-Plat Pat English Translation of JP 07-053950 A, published Feb. 28, 1995, 15 pages.

*Primary Examiner* — Taofiq A Solola

(74) *Attorney, Agent, or Firm* — Stinson Leonard Street LLP

(57) ABSTRACT

The present invention generally relates to various dibenzothiophene compounds, processes for preparing these compounds, and use of these compounds in organic light-emitting diodes and as cellular imaging agents. In particular, the compounds of the present invention include various sulfoxide and sulfone analogs of various dibenzothiophene compounds. The present invention also relates to cell imaging agents comprising one or more of the dibenzothiophene compounds and processes for imaging a cell using the compounds. The present invention also relates to organic light-emitting diodes comprising one or more of the dibenzothiophene compounds and processes for preparing these organic light-emitting diodes.

25 Claims, 9 Drawing Sheets

DIBENZOTHIOPHENE COMPOUNDS

REFERENCE TO RELATED APPLICATIONS

This application claims benefit of U.S. provisional application Ser. No. 62/574,431, filed Oct. 19, 2017, and U.S. provisional application Ser. No. 62/500,909, filed May 3, 2017, the entire disclosures of which are incorporated herein by reference.

STATEMENT REGARDING FEDERALLY SPONSORED RESEARCH OR DEVELOPMENT

This invention was made with Government support under grant CHE-1255270 awarded by the National Science Foundation. The Government has certain rights in the invention.

FIELD OF THE INVENTION

The present invention generally relates to various dibenzothiophene compounds, processes for preparing these compounds, and use of these compounds in organic light-emitting diodes and as cellular imaging agents. In particular, the compounds of the present invention include various sulfoxide and sulfone analogs of various dibenzothiophene compounds. The present invention also relates to cell imaging agents comprising one or more of the dibenzothiophene compounds and processes for imaging a cell using the compounds. The present invention also relates to organic light-emitting diodes comprising one or more of the dibenzothiophene compounds and processes for preparing these organic light-emitting diodes.

BACKGROUND OF THE INVENTION

Unsymmetrical dibenzothiophene sulfonate esters are key intermediates in the production of photoactive dibenzothiophene-S-oxide (DBTO) analogs which release ground state atomic oxygen [O($^3$P)] and are useful for organic light-emitting diodes (OLEDs).[1] Dibenzothiophene (DBT) derivatives per their oxidized form as DBTO or dibenzothiophene-S—S-dioxide (DBTOO) have displayed a history of varied photochemistry with the addition of a variety of substituents and different degrees of oxidation about the thiophene sulfur.[2] Various symmetrical DBTO derivatives have shown intriguing oxidative capabilities with small organic molecules, and more recently, with biomolecules.[3-5] Symmetrical DBTO derivatives have met some limitations in cellular studies prompting the development of unsymmetrical dibenzothiophenes (DBTs). Converting the sulfonate ester of an unsymmetrical DBT to the sulfonic acid salt elicits strong water solubility for an otherwise nonpolar molecule. Previous attempts to develop various dibenzothiophene sulfonic acids without protection of the acid are troublesome as the sensitivities of common carbon-carbon coupling reactions force a less direct synthetic pathway. Thus a need remains for photoactive unsymmetrical DBTs and efficient processes for producing these compounds

BRIEF SUMMARY OF THE INVENTION

The present invention generally relates to various dibenzothiophene compounds, processes for preparing these compounds, and use of these compounds in organic light-emitting diodes and as cellular imaging agents. Various dibenzothiophene compounds of the present invention include those having the structure of Formula (I) or Formula (II) or a salt thereof:

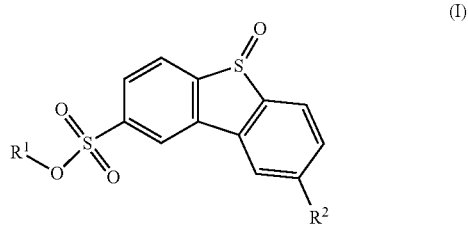

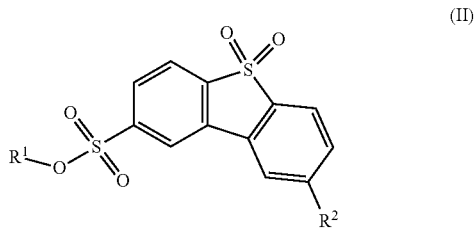

wherein each $R^1$ is independently hydrogen, substituted or unsubstituted aryl or substituted or unsubstituted heteroaryl; and each $R^2$ is independently substituted or unsubstituted aryl or substituted or unsubstituted heteroaryl. The present invention also relates to various processes for preparing these compounds.

The present invention also relates to various organic light-emitting diodes (OLEDs). These OLEDs generally include a first electrode; a second electrode; and an emissive layer positioned between the first electrode and the second electrode, wherein the emissive layer comprises one or more compounds of Formulas (I) and/or (II).

The present invention also relates to imaging agents useful for visualizing a cell. The imaging agents can comprise one or more compounds of Formulas (I) and/or (II). Further, the present invention relates to processes of visualizing a cell comprising applying the imaging agent to the cell, applying a luminescent probe (e.g., light) to stimulate the emission of a luminescent signal from the imaging agent, and detecting the signal.

Other objects and features will be in part apparent and in part pointed out hereinafter.

BRIEF DESCRIPTION OF THE SEVERAL VIEWS OF THE DRAWING

FIG. 6 presents a graph of an excitation scan of compound 8a.

FIG. 11 presents a graph of an UV absorbance of compound 8a.

DETAILED DESCRIPTION OF THE INVENTION

Figure 1:
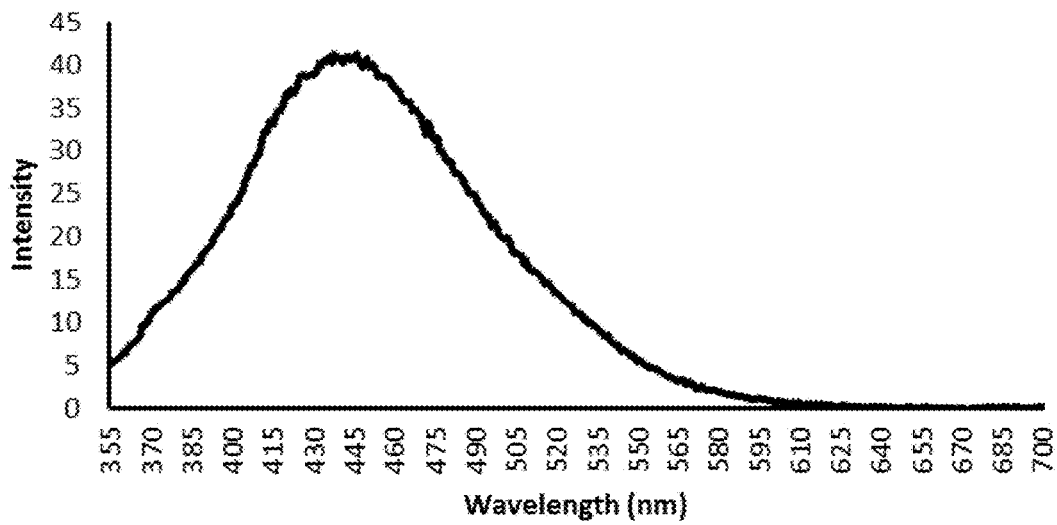
FIG. 1 presents a graph of an emission scan of compound 6b starting at 340 nm.
Figure 2:
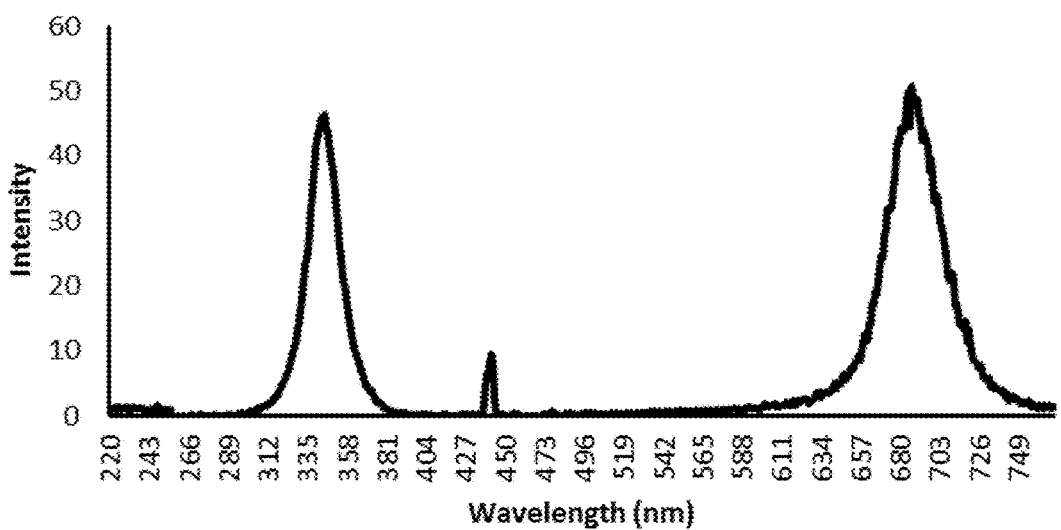
FIG. 2 presents a graph of an excitation scan of compound 6b.
Figure 3:
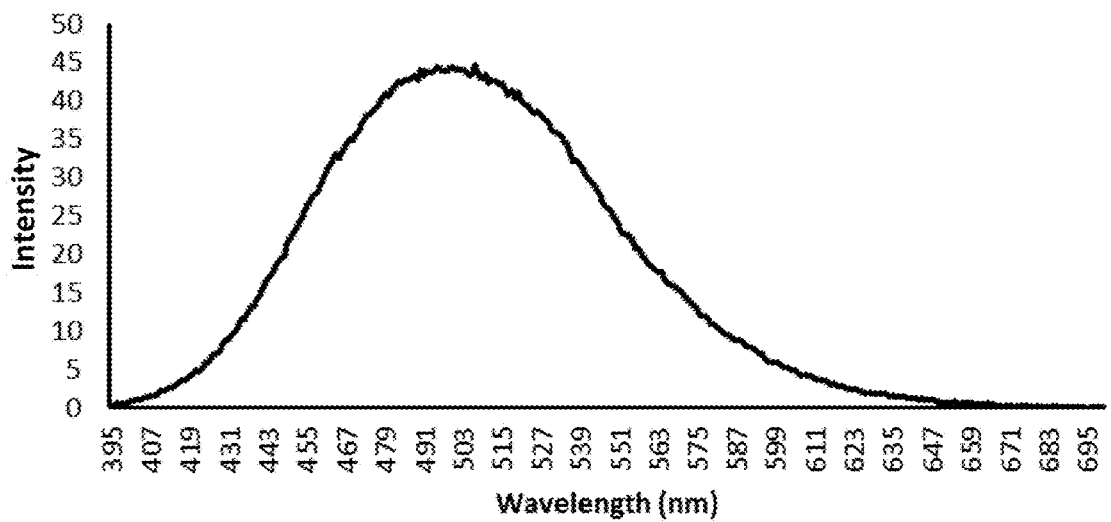
FIG. 3 presents a graph of an emission scan of compound 7b starting at 370 nm.
Figure 4:
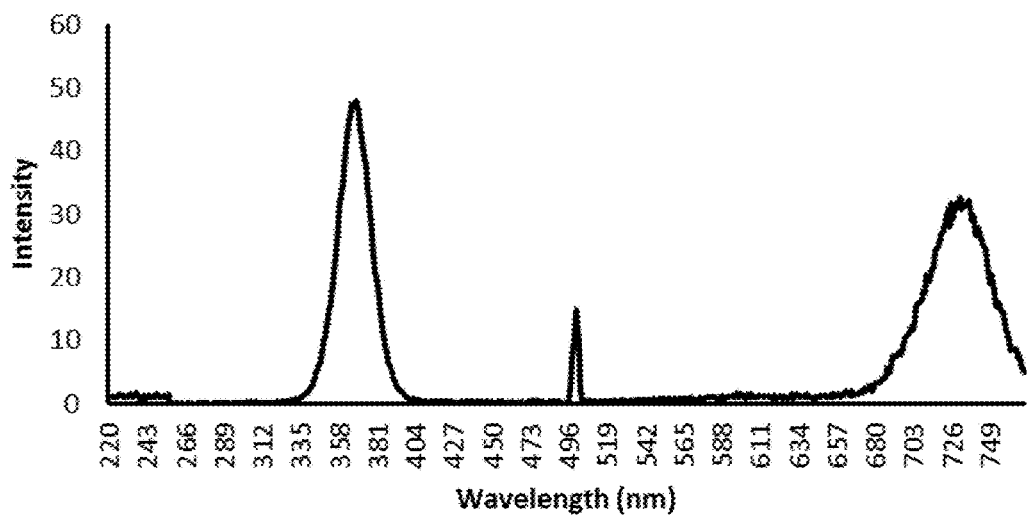
FIG. 4 presents a graph of an excitation scan of compound 7b.
Figure 5:
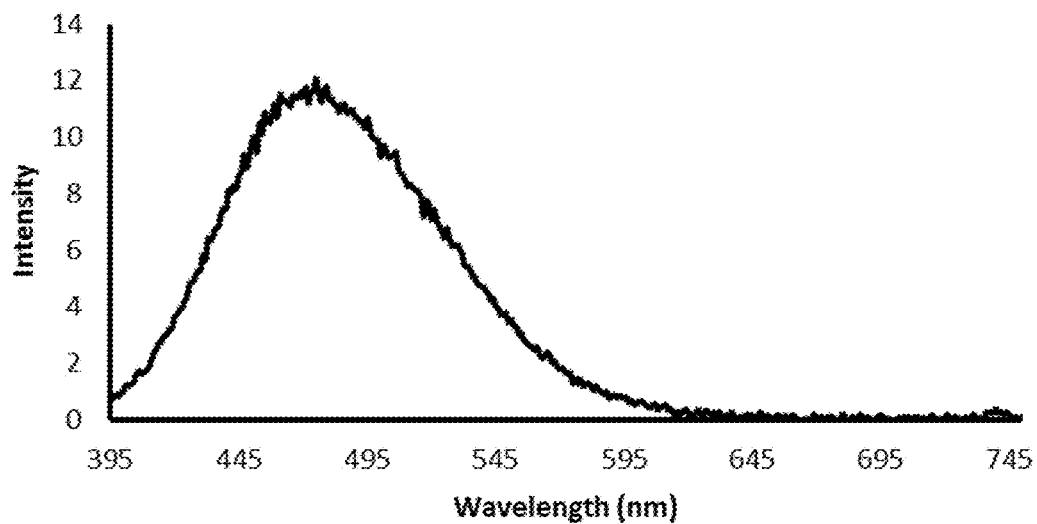
FIG. 5 presents a graph of an emission scan of compound 8a starting at 370 nm.
Figure 6:
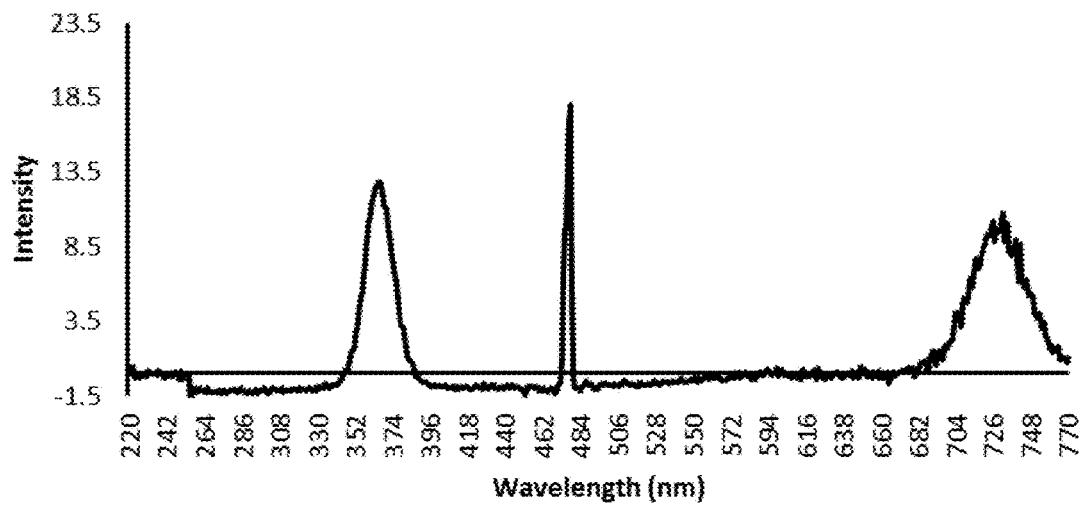
Figure 7:
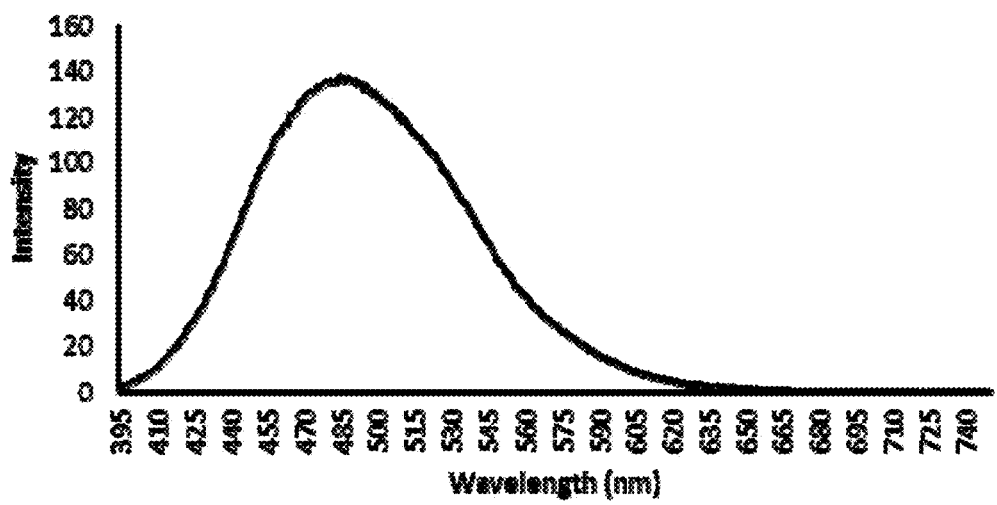
FIG. 7 presents a graph of an emission scan of compound 8b starting at 370 nm.
Figure 8:
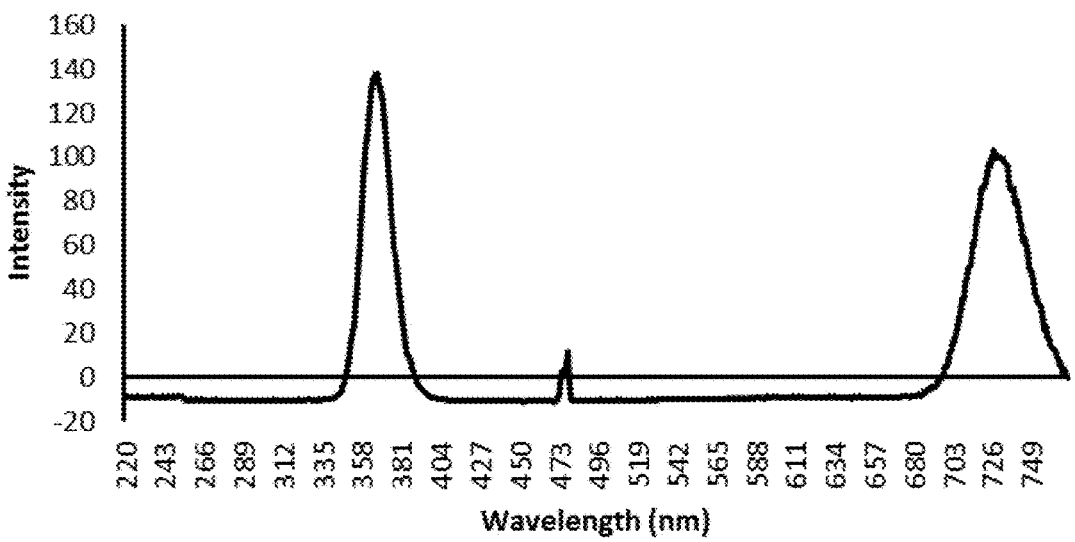
FIG. 8 presents a graph of an excitation scan of compound 8b.
Figure 9:
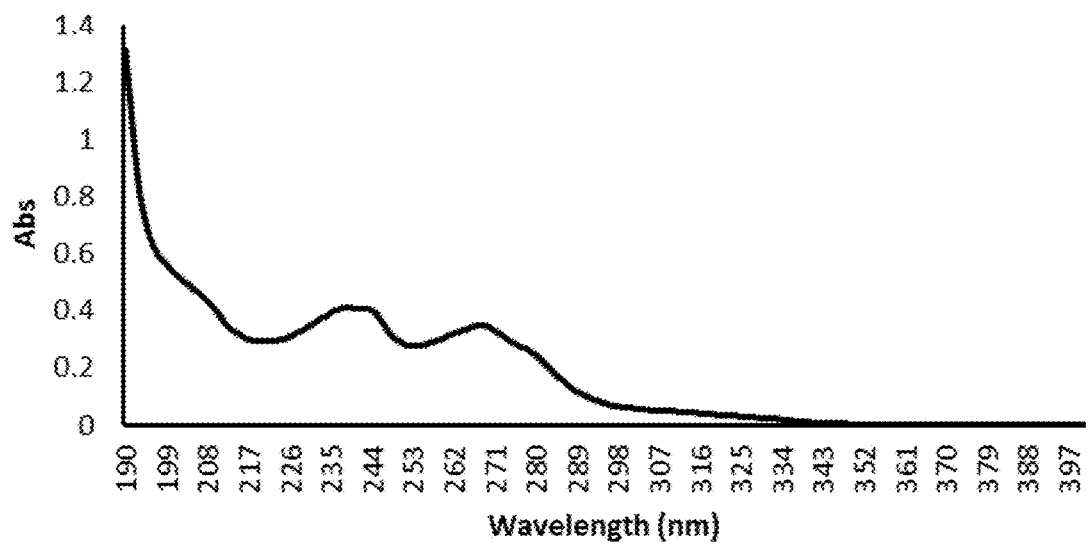
FIG. 9 presents a graph of an UV absorbance of compound 6b.
Figure 10:
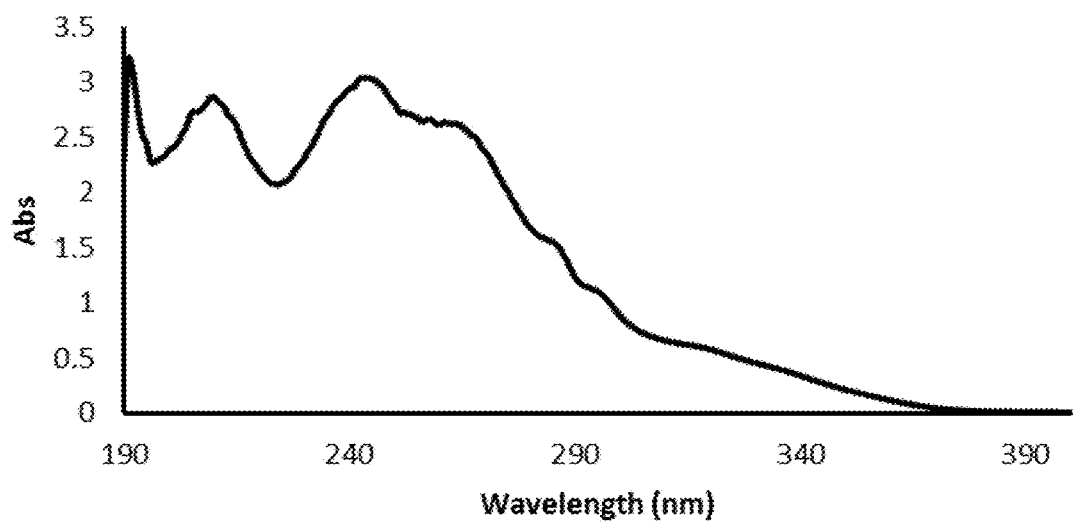
FIG. 10 presents a graph of an UV absorbance of compound 7b.
Figure 11:
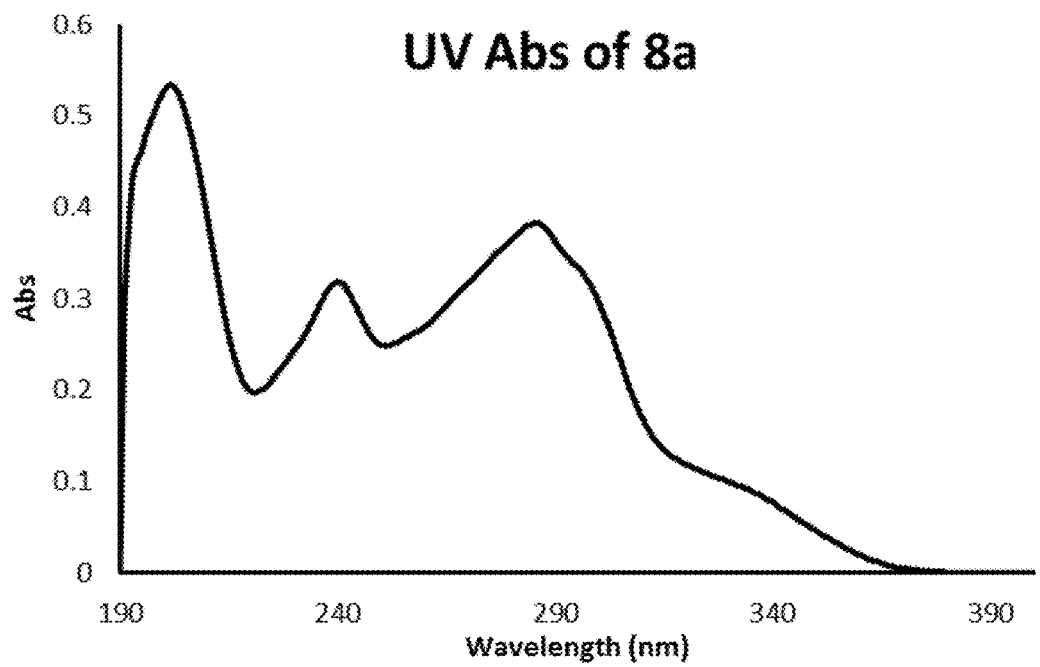
Figure 12:
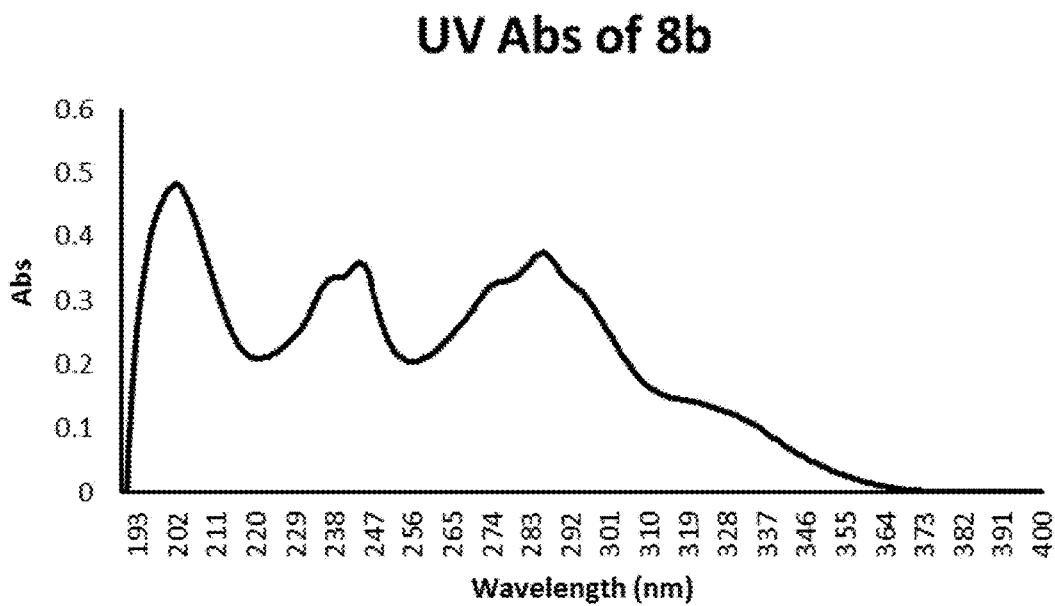
FIG. 12 presents a graph of an UV absorbance of compound 8b.

In general, the present invention is directed to various dibenzothiophene compounds, processes for preparing these compounds, and use of these compounds in organic light-emitting diodes and as cellular imaging agents. In particular, the compounds of the present invention include various sulfoxide and sulfone analogs of various dibenzothiophene compounds. The present invention also relates to organic light-emitting diodes comprising one of more of the dibenzothiophene compounds and processes for preparing these organic light-emitting diodes as well as processes for using these compounds as cellular imaging agents.

In various aspects, the present invention is directed to compounds having the structure of Formula (I) or Formula (II) or salt thereof:

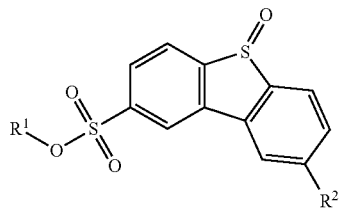

(I)

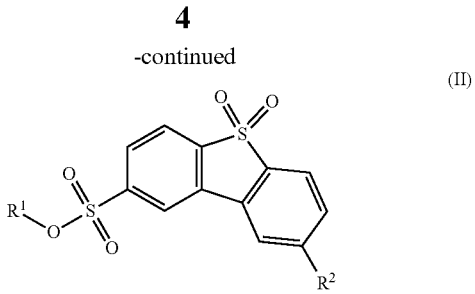

(II)

wherein each $R^1$ is independently hydrogen, substituted or unsubstituted aryl or substituted or unsubstituted heteroaryl; and each $R^2$ is independently substituted or unsubstituted aryl or substituted or unsubstituted heteroaryl. In various embodiments, the substituted aryl and the substituted heteroaryl comprise one or more substituents selected from the group consisting of hydroxy, oxo, halo, amino, substituted or unsubstituted $C_1$-$C_{20}$ alkyl, substituted or unsubstituted $C_1$-$C_{20}$ alkoxy, $C_1$-$C_{20}$ haloalkyl, $C_1$-$C_{20}$ haloalkoxy, and combinations thereof. In certain embodiments, the substituted or unsubstituted heteroaryl comprises a substituted or unsubstituted nitrogen-containing heteroaryl (e.g., pyrazole, imidazole, triazole, tetrazole, pyridine, pyridazine, pyrimidine, pyrazine, and triazine).

In various embodiments, each $R^1$ is independently hydrogen, substituted or unsubstituted phenyl, substituted or unsubstituted biphenyl, substituted or unsubstituted naphthyl, or substituted or unsubstituted anthracenyl. In some embodiments, each $R^1$ is independently hydrogen, phenyl, hydroxyphenyl, ethylphenyl, carboxyphenyl, naphthyl, anthracenyl, biphenyl, tolyl, cumyl, styryl, ortho-xylyl, meta-xylyl, para-xylyl, fluorophenyl, chlorophenyl, bromobenzyl, or iodobenzyl. In certain embodiments, each $R^1$ is independently hydrogen or a 5- or 6-membered aromatic ring (e.g., phenyl). In further embodiments, each $R^1$ is independently hydrogen, phenyl, biphenyl, or naphthyl. In further embodiments each $R^1$ is independently hydrogen or phenyl.

In various embodiments, each $R^2$ is independently substituted or unsubstituted phenyl, substituted or unsubstituted biphenyl, substituted or unsubstituted naphthyl, or substituted or unsubstituted anthracenyl. In some embodiments, each $R^2$ is independently phenyl, hydroxyphenyl, ethylphenyl, carboxyphenyl, naphthyl, anthracenyl, biphenyl, tolyl, cumyl, styryl, ortho-xylyl, meta-xylyl, para-xylyl, fluorophenyl, chlorophenyl, bromobenzyl, or iodobenzyl. In certain embodiments, each $R^2$ is independently a 5- or 6-membered aromatic ring (e.g., phenyl). In further embodiments, each $R^2$ is independently phenyl, biphenyl, or naphthyl.

In various embodiments, the compound of Formula (I) is selected from the group consisting of:

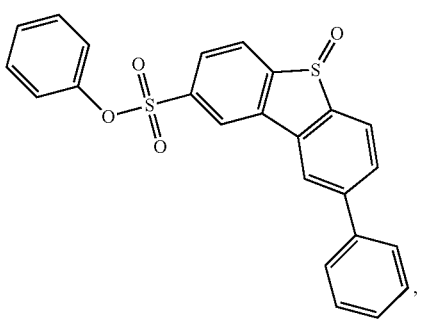

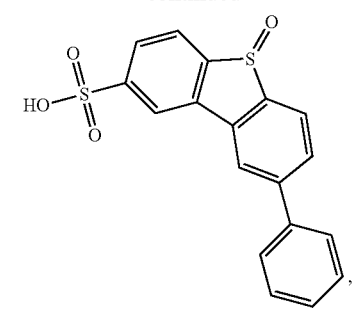
,
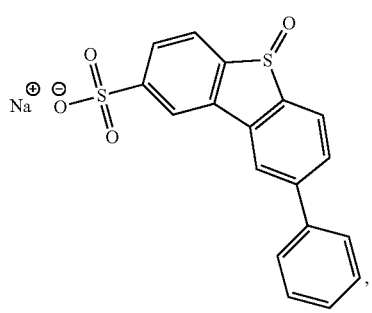
,
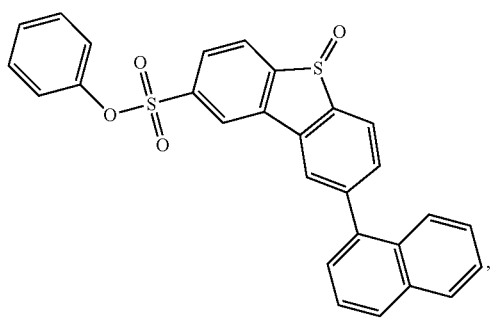
,
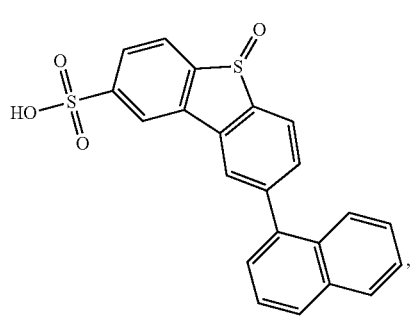
,
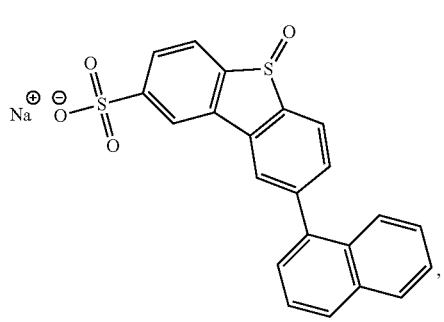
,
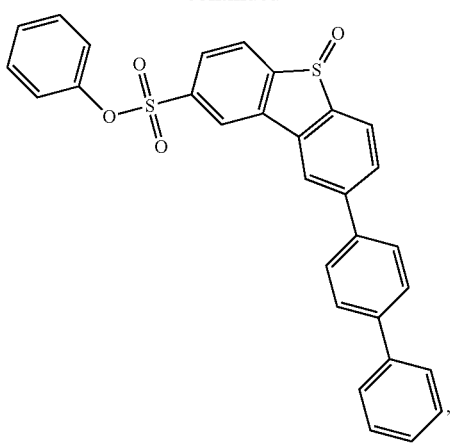
,
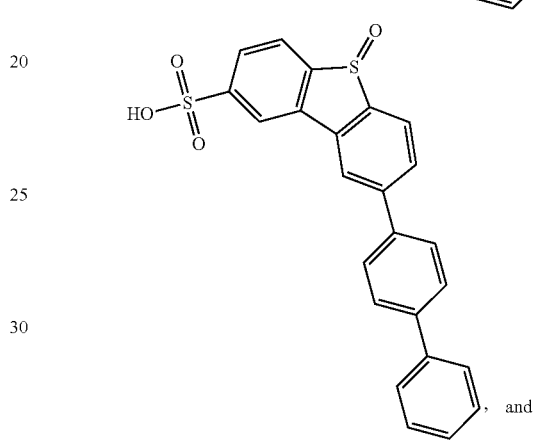
, and
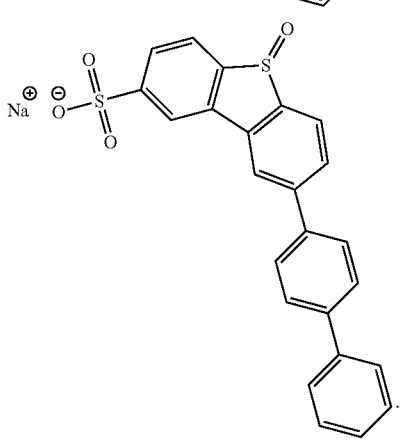
.
In various embodiments, the compound of Formula (II) is selected from the group consisting of:
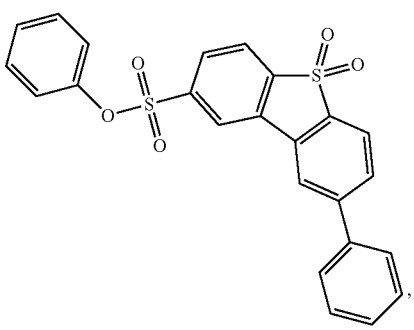
,

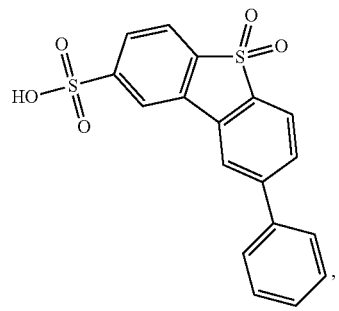

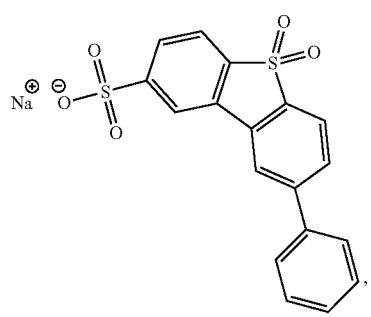

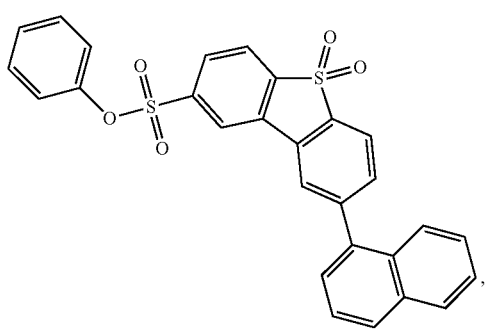

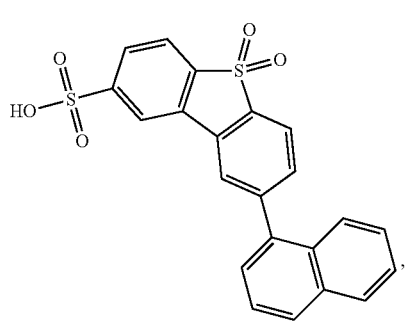

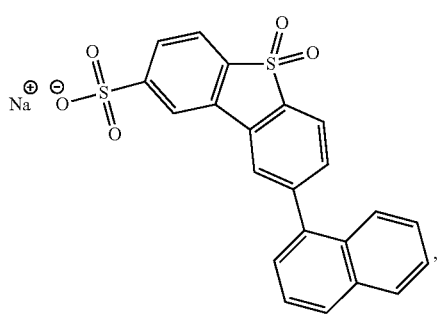

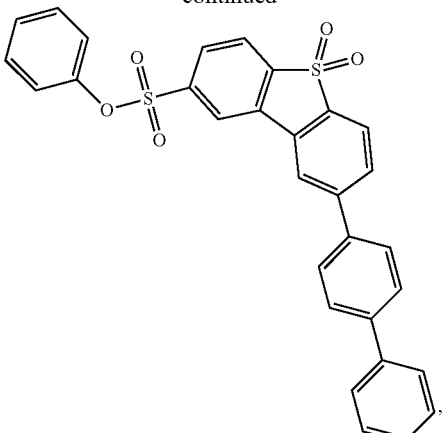

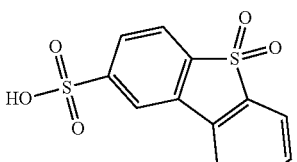

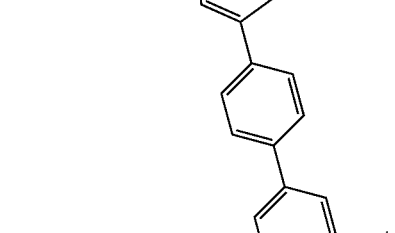, and

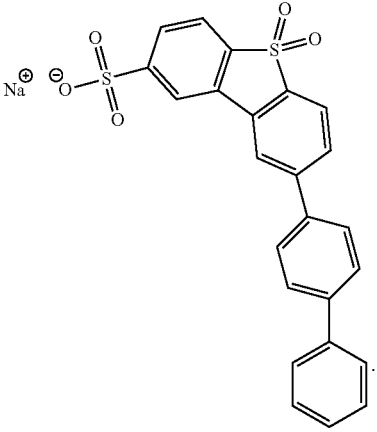

As noted, the present invention also relates to processes for preparing the compounds of Formulas (I) and (II). Various processes for preparing the compounds of Formulas (I) and (II) use dibenzothiophene as the starting material and proceed through a phenyl sulfonate ester of dibenzothiophene. The robust and unreactive nature of the phenyl sulfonate ester withstands a variety of reaction conditions while not interfering with the chemical processes.[6] The phenyl sulfonate analog of monobrominated dibenzothiophene (2-BrDBT) provides a platform by which alkyl, aryl, and vinylic substituents may be coupled to the DBT by virtue of Suzuki coupling. Coupling aromatic and aliphatic groups to DBTs has much value in the exploration of OLEDs as large DBT analogs are produced for their high triplet energy.[7] This growing field hosts tremendous potential in utilizing unsymmetrical DBT derivatives.[8,7,9,10] Unsymmetrical DBT derivatives boast untapped potential in OLEDs and selective biomolecule oxidation demanding elucidation of their synthesis which is henceforth detailed.

Various processes include reacting a compound of Formula (VIII):

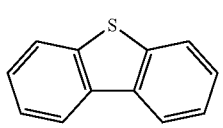

(VIII)

with a halogen source (e.g., diatomic halogens such as $Cl_2$ and $Br_2$ and other halogenating agents including N-halosuccinimides, such as N-bromosuccinimide) in the presence of a solvent (e.g., dimethylformamide) to form a compound of Formula (VII):

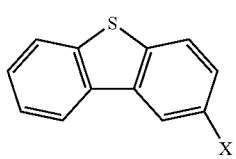

(VII)

wherein X is halogen (i.e., a halogen corresponding to the halogen source). Typically, the reaction of the compound of structure Formula (VII) with a sulfonic acid source is conducted at a temperature of from about −10° C. and about −5° C.

The processes can further comprise reacting the compound of Formula (VII), with a sulfonic acid source (e.g., halosulfonic acid, such as chlorosulfonic acid, sulfuric acid, sulfur trioxide, oleum, and mixtures thereof) in the presence of a solvent (e.g., dichloromethane) to produce a compound of Formula (VI):

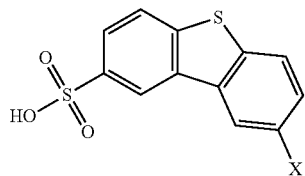

(VI)

wherein X is as defined above for Formula (VII).

Various processes further comprise reacting the compound of Formula (VI) with a thionyl halide (e.g., thionyl chloride) in the presence of a solvent (e.g., dimethylformamide) to produce a compound of Formula (V),

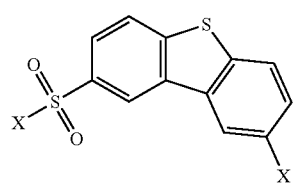

(V)

wherein each X is independently a halogen (e.g., chlorine or bromine).

Various processes further comprise reacting a compound of Formula (V) with a substituted or unsubstituted aryl alcohol or substituted or unsubstituted heteroaryl alcohol (e.g., phenol) in the presence of a bicyclic amine catalyst to produce a compound of Formula (IV):

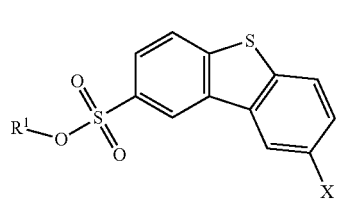

(IV)

wherein $R^1$ is substituted or unsubstituted aryl or substituted or unsubstituted heteroaryl and X is halogen. Generally, the substituted or unsubstituted aryl alcohol or substituted or unsubstituted heteroaryl alcohol reactant includes the moiety corresponding to the $R^1$ substituent.

In some embodiments, the bicyclic amine catalyst comprises 1,4-diazabicyclo[2.2.2]octane.

Various processes further comprise reacting a compound of Formula (IV) with a boronic acid in the presence of catalyst comprising a transition metal and a solvent (e.g., dimethoxyethane, ethanol, dioxane, water, toluene, methanol, and combinations thereof), under basic conditions to produce a compound of Formula (III):

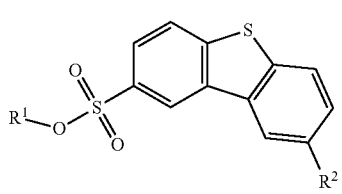

(III)

wherein $R^1$ and $R^2$ are each independently substituted or unsubstituted aryl or substituted or unsubstituted heteroaryl. In some embodiments, the boronic acid is phenylboronic acid, naphthylboronic acid, or biphenylboronic acid.

In some embodiments, the catalyst comprising a transition metal is a homogeneous catalyst. In various embodiments, the transition metal comprises a noble metal. In certain embodiments, the transition metal comprises a noble metal selected from the group consisting of palladium, platinum, and a combination thereof. Examples of the catalyst are be bis(triphenylphosphine)-palladium(II) dichloride ($PdCl_2$ $(PPh_3)_2$) or tetrakis(triphenylphosphine)palladium(0) (Pd $(PPh_3)_4$ [SPhos]).

Various processes further comprise reacting a compound of Formula (III) with a peroxy acid (e.g., m-chloroperoxybenzoic acid) in the presence of a solvent (e.g., dichloromethane) to form a compound of Formulas (I) and/or (II):

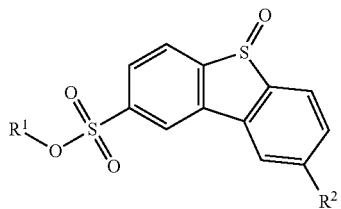

(I)

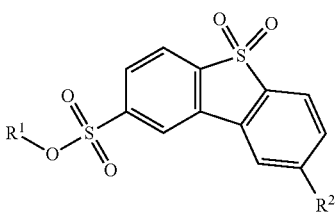

(II)

wherein each R¹ and R² are independently substituted or unsubstituted aryl or substituted or unsubstituted heteroaryl.

Various processes further comprise reacting a compound of Formula (I) or (II) with an amount of NaOH (e.g., 2M in methanol) in the presence of a solvent (e.g., dichloromethane) to produce a compound of Formula (IX) or (X), or salt thereof, wherein Formulas (I) and (II) have the structures of:

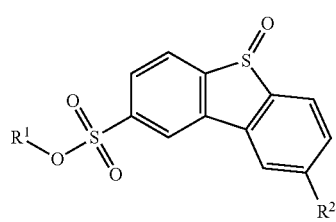

(I)

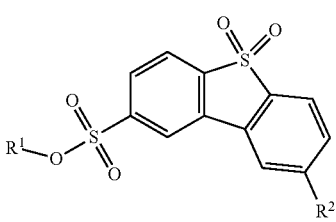

(II)

wherein R¹ and R² are each independently substituted or unsubstituted aryl or substituted or unsubstituted heteroaryl, and wherein the compounds of Formulas (IX) and (X) have the structures of:

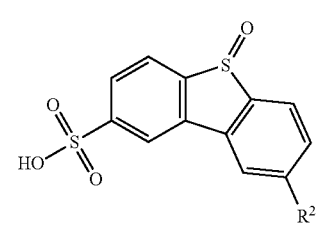

(IX)

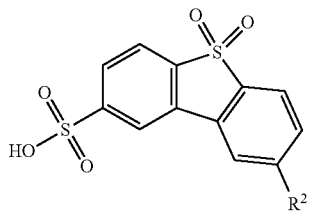

(X)

wherein each R² is independently substituted or unsubstituted aryl or substituted or unsubstituted heteroaryl.

In various embodiments, R¹ is phenyl and R² is phenyl, biphenyl, or naphthalene.

As noted, the invention also relates to organic light-emitting diodes (OLEDs). In some embodiments, the OLEDs are capable of producing blue or near blue light when irradiated with ultraviolet light.

In accordance with the present invention, the OLED comprises a first electrode, a second electrode, and an emissive layer positioned between the first electrode and the second electrode, wherein the emissive layer comprises a compound of Formulas (I) and/or Formula (II) or a salt thereof:

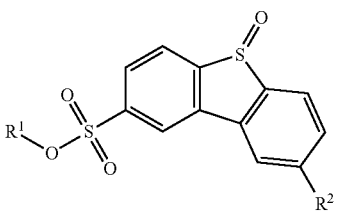

(I)

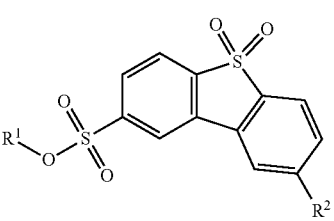

(II)

wherein each R¹ is independently hydrogen, substituted or unsubstituted aryl or substituted or unsubstituted heteroaryl; and each R² is independently substituted or unsubstituted aryl or substituted or unsubstituted heteroaryl.

In some embodiments, one of the first electrode and the second electrode may comprise a cathode and the other of the first electrode and the second electrode may comprise an anode. The OLED can further comprise one or more conductive layers, other emissive layers, hole transport layers, electron transport layers, and substrate layers.

The OLED of the present invention may be used in any device requiring or comprising an OLED. In various embodiments, the OLED may be incorporated into a display. For example, a display may comprise the OLED as described above. The display may be incorporated into a variety of additional devices. For example, the OLED may be incorporated into a display in a vehicle, a display in a television, a display in a computer, or a display in a mobile phone. The OLED may further be incorporated into a printer, a screen, a sign, a billboard, a telecommunications device, a telephone, or a wall, theater, or stadium screen.

The present invention also includes processes for preparing an organic light-emitting diode. In these processes, a first electrode is formed on a substrate, an emissive layer comprising one or more compounds of Formula (I) and Formula (II), as described in detail above, is formed, and a second electrode is formed. The emissive layer is positioned between the first electrode and the second electrode The present invention is also directed to imaging agents comprising one or more compounds of Formula (I) and/or Formula (II), or a salt thereof as defined herein.

The imaging agents can be used to stain a cell for imaging using standard microscopy techniques measuring luminescence known in the art. In some embodiments, the imaging agents are applied to a living cell. In various embodiments, the imaging agents are applied to a fixed cell. In various embodiments the imaging agents are applied for a length of time (e.g., incubation time) to the cell. In further embodiments, the incubation time can be between 30 minutes to about 4 hours (e.g., about 3 hours).

Any imaging technique capable of detecting fluorescence or phosphorescence known in the art may be used to detect the imaging agents. In some embodiments, cells can be imaged using microscopy using a luminescent probe (e.g., light) that excites the compounds described herein, resulting in the release of light of a certain wavelength that can then be detected. In various embodiments the emitted light is detected by a microscope and/or computer having imaging software. In some embodiments, confocal microscopy may be used. The luminescent probe can be a light having an excitation wavelength that maximally excites the compound, causing maximal luminescent emission. For example, the excitation wavelength can be between 200 and 300 nm, between 250 and 290 nm, or between 265 and 290 nm. In some embodiments, the excitation wavelength can be about 268 nm, about 274 nm, about 283 nm, or about 287 nm. In various embodiments, the excitation source is a laser.

When excited by the luminescent probe having the excitation wavelength described herein, the compounds comprising the imaging agent may emit light having an emission wavelength. The light having the emission wavelength can then be detected by a microscope and/or computer having imaging software calibrated to detect that wavelength. The compounds comprising the imaging agents described herein typically have an emission wavelength in the blue visible light range. Thus, the light having the emission wavelength can be detected visually through a microscope. The emission wavelength can range from about 350 nm to about 500 nm. In some embodiments, the emission wavelength can be between about 370 nm to about 495 nm. In certain embodiments, the emission wavelength can be about 371 nm, about 412 nm, about 421 nm, about 426 nm, about 485 nm, or about 492 nm.

The excitation and emission wavelengths chosen during a given imaging experiment should be optimized depending on experimental conditions. The experimental conditions are known to those skilled in the art and can include, but are not limited to, the solvents, media, temperature, and/or equipment (e.g., microscope, slides) chosen for the experiment. For example, the optimal excitation and emission wavelengths chosen for each compound can vary when the imaging agent is dissolved in ethanol compared to when it is dissolved in acetonitrile. The emission and excitation wavelengths described herein are meant to be illustrative and not limiting.

Unless otherwise indicated, the alkyl groups described herein are preferably lower alkyl containing from 1 to 20 carbon atoms in the principal chain. They may be straight chain, branched chain, or cyclic. Also, unless otherwise indicated, the substituted alkyl groups described herein can contain saturated or unsaturated and branched or unbranched carbon chains having from 1 to 20 carbon atoms in the principal chain.

EXAMPLES

The following non-limiting examples are provided to further illustrate the present invention.

Methods and Materials

Starting chemicals were obtained from commercial sources and utilized without further purification. All reactions were monitored by thin layer chromatography (TLC) and visualized by a UV lamp. Column chromatography was done using the BIOTAGE HORIZON using SORBTECH Flash Cartridges packed with SILLICYCLE SILIAFLASH 60 normal phase silica (230-400 mesh) with eluents noted in specific write-ups, all of which are reagent grade solvents. All of the products were characterized by NMR and high-resolution mass spectrometry (HRMS). $^1$H and $^{13}$C NMR were collected on either a BRUKER DRX-400 or an AGILENT 600 MHz DD2 while the FIRMS spectra were collected on a JOEL JMS-700 MS.

Example 1

The general synthetic route to unsymmetrical dibenzothiophene sulfonate esters is shown in Scheme 1. This method allowed the preparation of aryl, vinyl, and primary and secondary alkyl substituted dibenzothiophene sulfonate esters.

Scheme 1:

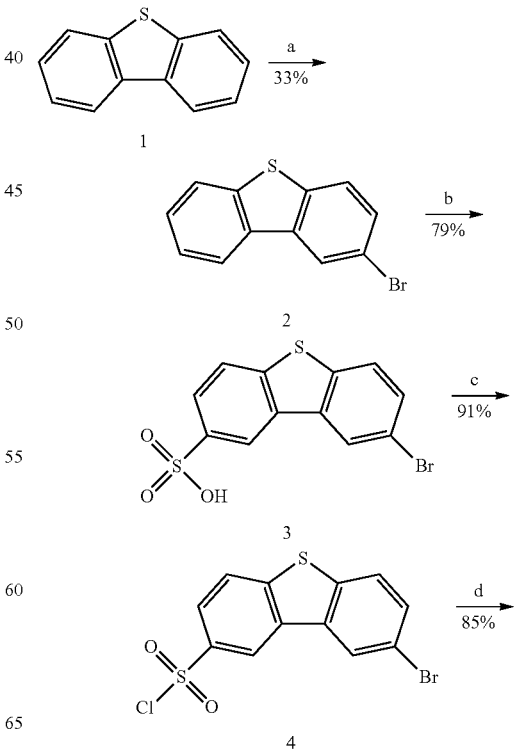

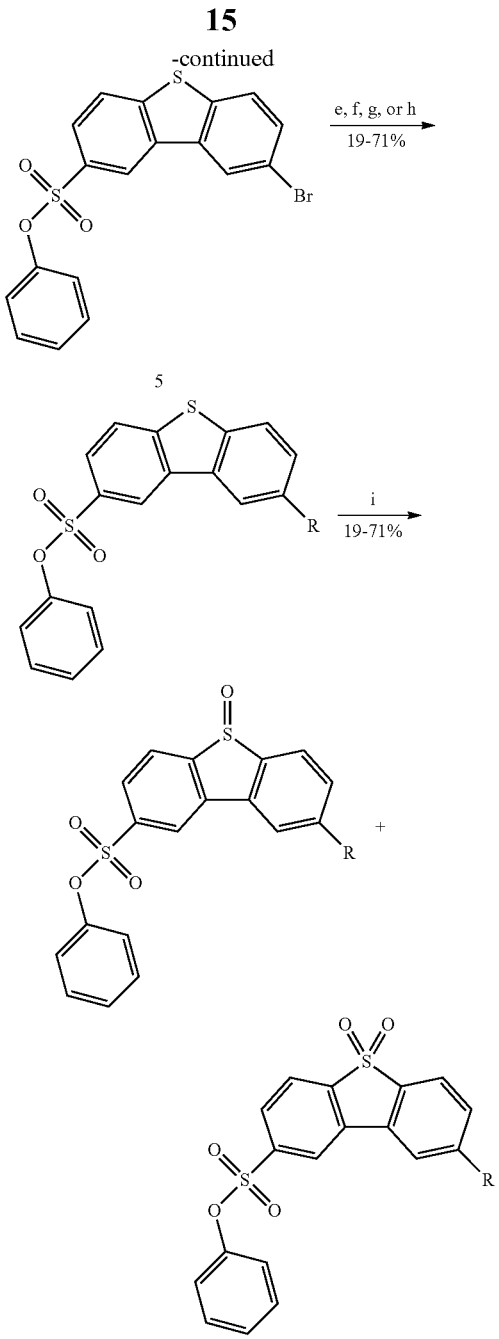

Reagents and conditions. (a) NBS, DMF, rt. (b) ClSO₃H, DCM, -5° C. (c) SOCl₂, DMF, reflux. (d) Phenol, DABCO, DCM, rt. (e) R = Primary Alkyl RB(OH)₂, Pd(dppf)Cl₂, K₃PO₄, Toluene, reflux. (f) R = Secondary Alkyl RB(OH)₂, PdCl₂(PPh₃)₂, KF, Toluene, reflux. (g) R = Aromatic ArB(OH)₂, PdCl₂(PPh₃)₂, NaB₄O₇, DME/H₂O (50/50), reflux. (h) R = Vinyl Pd(dba)₃, SPhos, K₃PO₄, Toluene/H₂O/MeOH (10/1/1.5), reflux. (i) mCPBA, DCM, -5° C.

The approach shown in Scheme 1 began with the addition of bromine to the 2 position of (1). Dibenzothiophene (1, 20.05 g, 0.1088 mol) and 200 mL DMF were added to a 500-mL round bottom flask. To the stirring reaction solution, a solution of N-Bromosuccinimide (NBS) (19.29 g, 0.1084 mol) dissolved in 100 mL DMF was slowly added. The combined solution was stirred for 48 hours, poured into 500 mL water and separated. The aqueous portion was then washed with CH₂Cl₂. The combined organic washes were collected, dried over MgSO₄, and evaporated under reduced pressure, producing a white solid. The solid was sequentially recrystallized in EtOH 5 times to yield a 9.6 g white solid containing 2-bromodibenzothiophene (2) in 33% yield and 95% purity (9.6 g 33%). $^1$H NMR (CHLOROFORM-d, 400 MHz): δ (ppm) 8.28 (d, J=1.8 Hz, 1H), 8.09-8.14 (m, 1H), 7.83-7.88 (m, 1H), 7.72 (d, J=8.4 Hz, 1H), 7.56 (dd, J=8.4, 1.8 Hz, 1H), 7.45-7.53 (m, 2H)

Next, 2-bromodibenzothiophene (2, 17.02 g, 0.0644 mol) and 300 mL HPLC grade CH₂Cl₂ were combined in a 500-mL round bottom flask and stirred into solution. The flask was then recessed in a cooling bath at -5° C. when a solution of ClSO₃H (3.94 ml, 0.0593 mol) and 100 mL HPLC CH₂Cl₂ was added dropwise via an addition funnel. When the addition was complete, the solution was allowed to warm to room temperature. The solution was then transferred into a freezer overnight. The solid was filtered over a glass frit and washed with liberal amounts of chilled CH₂Cl₂. The solid was then dried under vacuum for 24 hours. An off-white powder containing 8-bromodibenzo[b,d]thiophene-2-sulfonic acid (3) was afforded in 79% yield and greater than 90% purity as confirmed by $^1$HNMR (17.57 g, 79%). $^1$H NMR (DMSO-d₆, 400 MHz): δ (ppm) 8.66 (d, J=1.8 Hz, 1H), 8.58 (s, 1H), 8.00 (t, J=8.3 Hz, 2H), 7.79 (dq, J=8.3, 0.7 Hz, 1H), 7.67 (dd, J=8.6, 2.0 Hz, 1H) $^{13}$C NMR (DMSO-d₆, 101 MHz): δ (ppm) 145.6, 139.4, 138.0, 137.0, 133.3, 129.8, 125.5, 125.0, 124.9, 122.4, 119.3, 118.2 HRMS (FAB) m/z: [NaM+Na]+ calcd for C₁₂H₆BrO₃S₂: 386.873715; found: 386.8737.

The sulfonic acid was then converted to 8-bromodibenzo[b,d]thiophene-2-sulfonyl chloride (4). 8-bromodibenzo[b,d]thiophene-2-sulfonic acid (3, 7.69 g, 0.022 mol) and 150 mL thionyl chloride were combined in a 250-mL round bottom flask and stirred. To the mixture, 0.5 mL DMF was added. The reaction was refluxed for 24 hours. The reaction solution was then poured over 1 L crushed ice and stirred until the bubbling ceased and the yellowish solid stopped precipitating. The aqueous mixture was washed with dichloromethane (3×500 mL) then dried with MgSO₄. The solvent was evaporated under reduced pressure yielding a yellow-tinted solid. The crude solid was purified on a normal phase preparative column using dichloromethane as the eluent, producing a white powder containing 8-bromodibenzo[b,d]thiophene-2-sulfonyl chloride (4) with 99% purity (5.5 g, 91%). $^1$H NMR (DMSO-d₆, 400 MHz): δ (ppm) 8.66 (d, J=1.7 Hz, 1H), 8.57-8.59 (m, 1H), 7.97-8.03 (dd, 2H), 7.79 (dd, J=8.3, 1.7 Hz, 1H), 7.67 (dd, J=8.6, 2.0 Hz, 1H) $^{13}$C NMR (DMSO-d₆, 101 MHz): δ (ppm) 145.6, 139.4, 138.0, 137.0, 133.2, 129.7, 125.5, 125.0, 124.8, 122.4, 119.3, 118.2 HRMS (FAB) m/z: [M]+ calcd for C₁₂H₆BrClO₂S₂: 359.868113; found: 359.86813.

The sulfonate ester (5) was produced by the addition of phenol and DABCO to a solution of (4) in DCM at room temperature. 8-bromodibenzo[b,d]thiophene-2-sulfonyl chloride (4, 1.497 g, 0.004 mol) was dissolved in 350 mL DCM. To the solution, phenol (397 mg, 0.004 mol) was added. A separate solution of DABCO (531.6 mg, 0.0047 mol) and DCM was added to the initial solution. The combined reaction solution was stirred for an hour while monitored by TLC. After the reaction was complete, the solution was concentrated under reduced pressure producing a yellowish solid. The solid was purified by normal phase flash chromatography using ethyl acetate as the eluent, producing a white solid containing phenyl 8-bromodibenzo[b,d]thiophene-2-sulfonate (5) (1467.6 mg 0.0035 mol) in 85% yield following concentration under reduced pressure. $^1$H NMR (DMSO-d₆, 400 MHz): δ (ppm) 9.09 (s, 1H), 8.99 (s, 1H), 8.34 (dd, J=8.6, 1.7 Hz, 1H), 8.10 (dd, 1.5 Hz, 1H), 7.92 (dd, 1.5 Hz, 1H), 7.76 (dd, 1.5 Hz, 1H), 7.32-7.40 (m, 2H), 7.26-7.32 (m, 1H), 7.06-7.12 (m, 2H) $^{13}$C NMR (DMSO-d$_6$, 101 MHz): δ (ppm) 149.1, 145.8, 138.3, 135.9, 134.4, 131.2, 130.9, 130.1, 127.5, 126.0, 125.9, 125.2, 124.5, 123.0, 122.1, 118.8 HRMS (FAB) m/z: [M+Na]+ calcd for C$_{18}$H$_{11}$BrO$_3$S$_2$: 440.923070; found: 440.9231.

Alternate approaches to synthesize unsymmetrical DBTs did not produce isomerically pure product. Adding the hydrocarbon substituent to compound 1 followed by the addition of the sulfonic acid produced an unsymmetrical DBT; however, during the addition of the sulfonic acid, there were multiple sites of addition about the DBT. These isomers cannot be easily separated on a preparative scale. The coupling of compound 5 to different hydrocarbon substituents was achieved by the quintessential Suzuki coupling. This reaction was optimized for primary alkyl, secondary alkyl, aryl, and vinylic substituents. No single set of reaction conditions was capable of providing optimized yields for the different substituents. Each substituent required a particular set of reaction conditions to achieve the optimal yield. Thus, the reaction optimization was required for each substituent.

Table 1 provides a list of conditions used for the optimization of coupling aryl substituents to compound 5. Initial reaction probes were carried out using protocol a modified procedure from literature using SPhos as a co-ligand[11]. It was employed after the failure of Entry 5, which had previously been employed successfully on 2-bromodibenzothiophene. Entries 1-4 showed little success except with the second reaction, which produced a 48% yield according to GCMS. Thereafter, the catalyst loading and solvent system were manipulated until a satisfactory result was obtained.

yields of 35% and 65%, respectively. The detailed syntheses for these compounds are described below.

Scheme 2: Optimized aromatic coupling conditions.

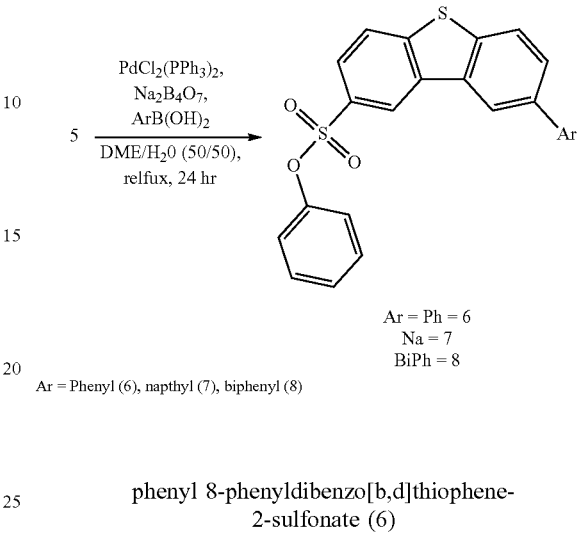

Ar = Phenyl (6), napthyl (7), biphenyl (8)

phenyl 8-phenyldibenzo[b,d]thiophene-2-sulfonate (6)

To a dry round bottom flask under inert atmosphere, phenyl 8-bromodibenzo[b,d]thiophene-2-sulfonate (5, 1.002 g, 0.0024 mol), Na$_2$B$_4$O$_7$ (1.450 g, 0.007 mol), PdCl$_2$(PPh$_3$)$_2$ (0.086 g, 0.00012 mol), and butylboronic acid

TABLE 1

Coupling of Aromatic and Vinyl Groups

| Entry | B(OH)$_2$ | Catalyst [Co-ligand] | Loading (mol %) | Base | Solvent System | Product | Yield |
|---|---|---|---|---|---|---|---|
| 1 | phenyl | PdCl$_2$(PPh$_3$)$_2$ [Sphos] | 5% [10%] | Na$_2$B$_4$O$_7$ | Dioxane/EtOH (5/1) | 6 | 0% |
| 2 | phenyl | PdCl$_2$(PPh$_3$)$_2$ [Sphos] | 5% [10%] | K$_2$CO$_3$ | DME/H$_2$O (50/50) | 6 | 48%$^a$ |
| 3 | phenyl | Pd(PPh$_3$)$_4$ [Sphos] | 3% [10%] | Na$_2$B$_4$O$_7$ | Dioxane/EtOH (4/1) | 6 | 0% |
| 4 | phenyl | Pd(PPh$_3$)$_4$ [Sphos] | 10% [10%] | Na$_2$B$_4$O$_7$ | DME/H$_2$O (50/50) | 6 | 0% |
| 5 | phenyl | Pd(PPh$_3$)$_4$ | 5% | K$_2$CO$_3$ | DME/H$_2$O (50/50) | 6 | 18% |
| 6 | phenyl | PdCl$_2$(PPh$_3$)$_2$ | 5% | K$_2$CO$_3$ | DME/H$_2$O (50/50) | 6 | 0%$^a$ |
| 7 | phenyl | PdCl$_2$(PPh$_3$)$_2$ | 5% | Na$_2$B$_4$O$_7$ | Dioxane/EtOH (5/1) | 6 | 0% |
| 8 | phenyl | PdCl$_2$(PPh$_3$)$_2$ | 3% | Na$_2$B$_4$O$_7$ | Dioxane/EtOH (4/1) | 6 | 0% |
| 9 | phenyl | PdCl$_2$(PPh$_3$)$_2$ | 5% | Na$_2$B$_4$O$_7$ | DME/H$_2$O (50/50) | 6 | 66%$^a$ |
| 10 | phenyl | PdCl$_2$(PPh$_3$)$_2$ | 5% | Na$_2$B$_4$O$_7$ | Dioxane/H$_2$O (5/1) | 6 | 69%$^a$ |
| 11 | phenyl | PdCl$_2$(PPh$_3$)$_2$ | 5% | KF | Toluene | 6 | 45%$^a$ |
| 12 | phenyl | PdCl$_2$(PPh$_3$)$_2$ | 5% | Na$_2$B$_4$O$_7$ | 6 | 6 | 71% |
| 13 | napthyl | PdCl$_2$(PPh$_3$)$_2$ | 5% | Na$_2$B$_4$O$_7$ | DME/H$_2$O (50/50) | 7 | 72% |
| 14 | biphenyl | PdCl$_2$(PPh$_3$)$_2$ | 5% | Na$_2$B$_4$O$_7$ | DME/H$_2$O (50/50) | 8 | 65% |
| 15 | trans-phenylvinyl | Pd(dba)$_3$ [Sphos] | 3% [4%] | K$_3$PO$_4$ | Toluene/H$_2$O/MeOH (10/1/1.5) | 9 | 31% |

$^a$Yield based on GCMS

For the coupling of aryl groups to compound 5 as shown in Scheme 2, the reaction conditions were bis(triphenylphosphine)palladium(II) dichloride [PdCl$_2$(PPh$_3$)$_2$] 5 mol % loading with three equivalents of Na$_2$B$_4$O$_7$ combined with 1.2 equivalents of phenyl boronic acid in DME and distilled water [1/1 (v/v)]. This set of reaction conditions initially produced a 66% yield per GCMS (Entry 9). Entry 10 provides better yield with 69%; however, the reaction mixer contained residual starting material (5) which proved to be difficult to separate from compound 6. The selected conditions, which were only analyzed by GCMS, were then repeated on the gram scale producing a 71% yield. The reaction was then carried out with naphthyl boronic acid and biphenyl boronic acid producing compounds 7 and 8 in (0.356 g, 0.0029 mol) were combined. 75 mL DME and nanopure water (1/1) were added to the flask after it had been degassed by nitrogen bubbling for 15 minutes. The solution was refluxed for 24 hours and then cooled to room temperature. The solution was then poured over 100 mL saturated ammonium chloride (aq). The bilayer was washed with DCM (3×150 mL). The organic washes were collected and concentrated under reduced pressure producing a dark grey solid. The crude solid was separated by normal phase flash chromatography using hexanes/ethyl acetate (9/1) as the eluent. The column produced a white solid after concentration under reduced pressure affording the product in 70% yield. (0.702 g, 0.017 mol). $^1$H NMR (DMSO-d$_6$, 400 MHz): δ (ppm) 9.21 (d, J=1.7 Hz, 1H), 9.05 (d, J=1.7 Hz, 1H), 8.34 (d, J=8.6 Hz, 1H), 8.21 (d, J=8.6 Hz, 1H), 7.88-7.99 (m, 4H), 7.53 (t, J=7.7 Hz, 2H), 7.33-7.44 (m, 3H), 7.25-7.32 (m, 1H), 7.07-7.13 (m, 2H) $^{13}$C NMR (DMSO-d$_6$, 101 MHz): δ (ppm) 149.1, 145.7, 139.4, 138.4, 137.6, 135.6, 134.8, 131.0, 130.1, 128.9, 127.7, 127.5, 127.1, 127.0, 125.6, 124.4, 123.7, 122.8, 122.1, 121.2 HRMS (FAB) m/z: [M+Na]+ calcd for C$_{24}$H$_{16}$O$_3$S$_2$: 439.043859; found: 439.04388.

phenyl 8-(napthalen-2-yl)dibenzo[b,d]thiopehen-2-sulfonate (7)

To a dry round bottom flask under inert atmosphere, phenyl 8-bromodibenzo[b,d]thiophene-2-sulfonate (5, 1.016 g, 0.0024 mol), Na$_2$B$_4$O$_7$ (1.439 g, 0.007 mol), PdCl$_2$(PPh$_3$)$_2$ (0.082 g, 0.00012 mol), and 2-Napthylboronic acid (0.498 g, 0.0029 mol) were combined. 50 mL DME and nanopure water (1/1) were added to the flask after it had been degassed by nitrogen bubbling for 15 minutes. The solution was refluxed for 24 hours and then cooled to room temperature. The solution was then poured over 150 mL saturated ammonium chloride (aq). The bilayer was washed with DCM (3×150 mL). The organic washes were collected and concentrated under reduced pressure producing a dark grey solid. The crude solid was separated by normal phase flash chromatography using hexanes/ethyl acetate (9/1) as the eluent. The brown solid resulting from the column was then recrystallized in 200 mL ethanol/toluene (3/1 v/v). The recrystallization produced a brown solid affording the product in 72% yield. (0.800 g, 0.017 mol) $^1$H NMR (DMSO-d$_6$, 400 MHz): δ (ppm) 9.25 (d, J=1.7 Hz, 1H), 9.20 (d, J=1.7 Hz, 1H), 8.49 (s, 1H), 8.36 (d, J=8.6 Hz, 1H), 8.27 (d, J=8.3 Hz, 1H), 8.14 (dd, J=8.4, 1.8 Hz, 2H), 8.03-8.09 (m, 2H), 7.97-8.01 (m, 1H), 7.91 (dd, J=8.6, 2.0 Hz, 1H), 7.57 (quind, J=7.1, 1.6 Hz, 2H), 7.34-7.40 (m, 2H), 7.26-7.31 (m, 1H), 7.13-7.26 (m, 1H), 7.08-7.13 (m, 2H) $^{13}$C NMR (DMSO-d$_6$, 151 MHz): δ (ppm) 149.1, 145.8, 138.6, 137.4, 136.7, 135.7, 134.9, 133.4, 132.4, 131.0, 130.1, 128.5, 128.2, 127.5, 127.5, 127.2, 126.5, 126.2, 125.6, 125.4, 124.5, 123.8, 122.8, 122.1, 122.1, 121.4 HRMS (FAB) m/z: [M+Na]+ calcd for C$_{28}$H$_{18}$O$_3$S$_2$: 489.059509; found: 489.05951.

phenyl 8-([1,1'-biphenyl]-4-yl)dibenzo[b,d]thiophene-2-sulfonate (8)

To a dry round bottom flask under inert atmosphere, phenyl 8-bromodibenzo[b,d]thiophene-2-sulfonate (5, 1.004 g, 0.0024 mol), Na$_2$B$_4$O$_7$ (1.473 g, 0.007 mol), PdCl$_2$(PPh$_3$)$_2$ (0.092 g, 0.00012 mol), and 4-Biphenylboronic acid (0.590 g, 0.0029 mol) were combined. 75 mL DME and nanopure water (1/1) were added to the flask after it had been degassed by nitrogen bubbling for 15 minutes. The solution was refluxed for 24 hours and then cooled to room temperature. The solution was then poured over 100 mL saturated ammonium chloride (aq). The bilayer was washed with DCM (3×150 mL). The organic washes were collected and concentrated under reduced pressure producing a dark grey solid. The crude solid was separated by normal phase flash chromatography using hexanes/ethyl acetate (9/1) as the initial eluent followed by pure ethyl acetate. The column produced an off-white solid after concentration under reduced pressure affording the product in 65% yield. (0.764 g, 0.016 mol) $^1$H NMR (DMSO-d$_6$, 400 MHz): δ (ppm) 9.24 (d, J=1.7 Hz, 1H), 9.12 (d, J=1.5 Hz, 1H), 8.35 (d, J=8.6 Hz, 1H), 8.23 (d, J=8.6 Hz, 1H), 8.01-8.08 (m, 3H), 7.91 (dd, J=8.4, 1.8 Hz, 1H), 7.82 (d, J=8.3 Hz, 2H), 7.76 (d, J=7.3 Hz, 2H), 7.51 (t, J=7.6 Hz, 2H), 7.33-7.43 (m, 3H), 7.26-7.32 (m, 1H), 7.07-7.13 (m, 2H) $^{13}$C NMR (DMSO-d$_6$, 101 MHz): δ (ppm) 149.1, 145.7, 139.6, 139.3, 138.5, 138.3, 137.0, 135.6, 134.8, 131.0, 130.1, 129.0, 127.6, 127.5, 127.1, 126.8, 126.6, 125.6, 124.4, 123.7, 122.8, 122.1, 121.0 HRMS (FAB) m/z: [M]+ calcd for C$_{30}$H$_{20}$O$_3$S$_2$: 492.085388; found: 492.08539.

Coupling of DBT to a vinylic group (Scheme 3) was also achieved using reaction conditions utilized in a parallel project within the group. Trans-phenylvinyl boronic in solution with Pd(dba)$_3$, SPhos, K$_3$PO$_4$ in Toluene/H2O/MeOH (10/1/1.5). This produced 99% pure product in 31% yield. Carbons hybridized as sp$^2$ have shown retarded coupling under standard Suzuki coupling conditions. The yield is acceptable as Suzuki coupling with DBTs has also shown hindered reactivity.[10] The detailed synthesis for this compound is described below.

Scheme 3: Optimized vinylic coupling conditions from trans-phenylvinyl (9)

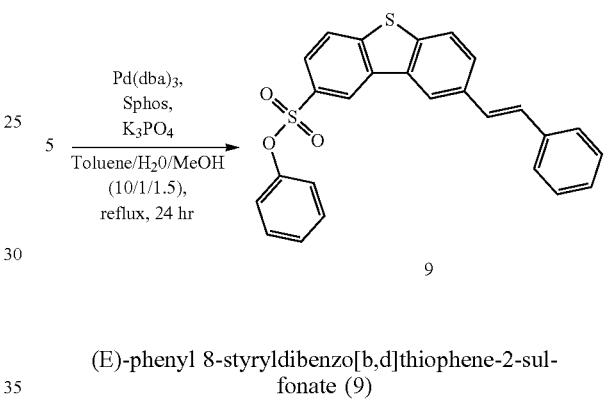

(E)-phenyl 8-styryldibenzo[b,d]thiophene-2-sulfonate (9)

To a dry round bottom flask under inert atmosphere, phenyl 8-bromodibenzo[b,d]thiophene-2-sulfonate (5, 1.004 g, 0.0024 mol), K$_3$PO$_4$ (1.549 g, 0.007 mol), Pd(dba)$_3$ (0.09 g, 0.0001 mol), SPhos (0.048 g, 0.001 mol) and trans-2-Phenylvinylboronic acid (0.590 g, 0.0029 mol) were combined. 75 mL toluene, nanopure water, and methanol (10/1/1.5) were added to the flask after it had been degassed by nitrogen bubbling for 15 minutes. The solution was refluxed for 24 hours and then cooled to room temperature. The solution was then poured over 100 mL saturated ammonium chloride (aq). The bilayer was washed with DCM (3×150 mL). The organic washes were collected and concentrated under reduced pressure producing a dark grey solid. The crude solid was separated by normal phase flash chromatography using ethyl acetate. The column produced an off-white solid. This solid was recrystallized in 500 mL ethanol affording the product in 31% yield. (0.324 g, 0.0007 mol) $^1$H NMR (DMSO-d$_6$, 400 MHz): δ (ppm) 9.02 (d, J=1.7 Hz, 1H), 8.95 (d, J=1.0 Hz, 1H), 8.35 (d, J=8.6 Hz, 1H), 8.13 (d, J=8.3 Hz, 1H), 7.91 (dd, J=8.6, 2.0 Hz, 1H), 7.85 (dd, J=8.4, 1.6 Hz, 1H), 7.65 (d, J=7.3 Hz, 2H), 7.54-7.61 (m, 1H), 7.34-7.47 (m, 5H), 7.27-7.33 (m, 2H), 7.07-7.11 (m, 2H) $^{13}$C NMR (DMSO-d$_6$, 101 MHz): δ (ppm) 149.1, 145.7, 138.3, 137.1, 135.4, 134.9, 134.5, 130.9, 130.1, 129.1, 128.8, 127.9, 127.8, 127.5, 127.4, 126.4, 125.6, 124.5, 123.4, 122.3, 122.1, 120.2 FIRMS (FAB) m/z: [M]+ calcd for C$_{26}$H$_{18}$O$_3$S$_2$: 442.069739; found: 442.06973.

The next series of reactions probed were aimed to couple primary alkyl chains to compound 5 according to Scheme 4. As length of the alkyl boronic acid increased, the isolated yield decreased from 60% to 19% (See Table 2, Entry 3-6), suggesting increased sterics associated with alkyl boronic acid were responsible for the decreased yields. The syntheses for these compounds are described in detail below.

Scheme 4: Optimized primary alkyl coupling conditions.

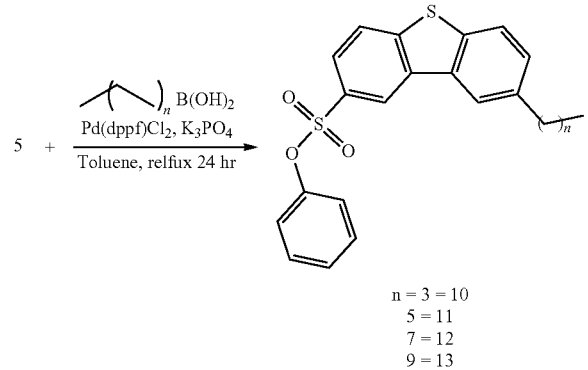

Butyl (10) (n = 3), hexyl (11) (n = 5), octyl (12) (n = 7), decyl (13) (n = 9).

TABLE 2

Coupling of Primary Alkyl Groups

| Entry | B(OH)$_2$ | Catalyst | Loading (mol %) | Base | Solvent System | Product | Yield |
|---|---|---|---|---|---|---|---|
| 1 | butyl | PdCl$_2$(PPh$_3$)$_2$ | 5% | Na$_2$B$_4$O$_7$ | DME/H$_2$0 (50/50) | 10 | 0% |
| 2 | butyl | Pd(dppf)Cl$_2$ | 20% | K$_3$PO$_4$ | Toluene | 10$^a$ | 57%$^a$ |
| 3 | butyl | Pd(dppf)Cl$_2$ | 20% | K$_3$PO$_4$ | Toluene | 10 | 60% |
| 4 | hexyl | Pd(dppf)Cl$_2$ | 20% | K$_3$PO$_4$ | Toluene | 11 | 48% |
| 5 | octyl | Pd(dppf)Cl$_2$ | 20% | K$_3$PO$_4$ | Toluene | 12 | 32% |
| 6 | decyl | Pd(dppf)Cl$_2$ | 20% | K$_3$PO$_4$ | Toluene | 13 | 20% |

$^a$Yield based on GCMS phenyl 8-butyldibenzo[b,d]thiophene-2-sulfonate (10)

To a dry round bottom flask under inert atmosphere, phenyl 8-bromodibenzo[b,d]thiophene-2-sulfonate (5, 1.002 g, 0.0024 mol), K$_3$PO$_4$ (1.012 g, 0.0047 mol), Pd(dppf)Cl$_2$ (0.356 g, 0.0004 mol), and butylboronic acid (0.294 g, 0.0029 mol) were combined. 100 mL toluene was added to the flask after it had been degassed by nitrogen bubbling for 15 minutes. The solution was refluxed for 24 hours and then cooled to room temperature. The solution was then poured over 100 mL saturated ammonium chloride (aq). The bilayer was washed with DCM (3×150 mL). The organic washes were collected and concentrated under reduced pressure, producing a dark grey solid. The crude solid was separated by normal phase flash chromatography using hexanes/ethyl acetate (9/1) as the eluent. The column produced a clear oil which crystallized at room temperature, affording the product in 60% yield. (0.565 g, 0.014 mol). $^1$H NMR (DMSO-d$_6$, 400 MHz): δ (ppm) 8.91 (s, 1H), 8.48 (s, 1H), 8.30 (d, J=8.6 Hz, 1H), 8.00 (d, J=8.3 Hz, 1H), 7.86 (dd, J=8.4, 1.6 Hz, 1H), 7.46 (d, J=8.1 Hz, 1H), 7.33-7.40 (m, 2H), 7.26-7.31 (m, 1H), 7.08 (d, J=8.1 Hz, 2H), 2.77 (t, J=7.7 Hz, 2H), 1.67 (quin, J=7.6 Hz, 2H), 1.35 (sxt, J=7.3 Hz, 2H), 0.93 (t, J=7.3 Hz, 3H) $^{13}$C NMR (DMSO-d$_6$, 101 MHz): δ (ppm) 149.1, 145.6, 140.1, 136.5, 135.4, 134.1, 130.7, 130.1, 129.2, 127.5, 125.2, 124.4, 122.9, 122.6, 122.1, 122.1, 34.6, 33.3, 21.8, 13.8 FIRMS (FAB) m/z: [M+Na]+ calcd for C$_{22}$H$_{20}$O$_3$S$_2$: 419.075159; found: 419.07516.

phenyl 8-hexyldibenzo[b,d]thiophene-2-sulfonate (11)

To a dry round bottom flask under inert atmosphere, phenyl 8-bromodibenzo[b,d]thiophene-2-sulfonate (5, 1.016 g, 0.0024 mol), K$_3$PO$_4$ (1.056 g, 0.0047 mol), Pd(dppf)Cl$_2$ (0.345 g, 0.0004 mol), and hexylboronic acid (0.320 g, 0.0029 mol) were combined. 100 mL toluene was added to the flask after it had been degassed by nitrogen bubbling for 15 minutes. The solution was refluxed for 24 hours and then cooled to room temperature. The solution was then poured over 100 mL saturated ammonium chloride (aq). The bilayer was washed with DCM (3×150 mL). The organic washes were collected and concentrated under reduced pressure, producing a dark grey solid. The crude solid was separated by normal phase flash chromatography using hexanes/ethyl acetate (9/1) as the eluent. The column produced a clear oil which crystallized at room temperature, affording the product in 48% yield. (0.497 g, 0.012 mol). $^1$H NMR (DMSO-d$_6$, 400 MHz): δ (ppm) 8.48 (d, J=1.0 Hz, 1H), 8.31 (d, J=8.6 Hz, 1H), 8.01 (d, J=8.3 Hz, 1H), 7.87 (dd, J=8.6, 2.0 Hz, 1H), 7.46 (dd, J=8.2, 1.6 Hz, 1H), 7.33-7.40 (m, 2H), 7.26-7.31 (m, 1H), 7.05-7.10 (m, 2H), 2.72-2.79 (m, 2H), 1.63-1.73 (m, 2H), 1.25-1.37 (m, 6H), 0.82-0.89 (m, 3H) $^{13}$C NMR (DMSO-d$_6$, 151 MHz): δ (ppm) 149.1, 145.6, 140.2, 136.6, 135.4, 134.1, 130.7, 130.1, 129.2, 127.5, 125.2, 124.4, 122.9, 122.6, 122.2, 122.1, 35.0, 31.1, 28.4, 22.1, 14.0 FIRMS (FAB) m/z: [M+Na]+ calcd for C$_{24}$H$_{24}$O$_3$S$_2$: 447.106459; found: 447.10648.

phenyl 8-octyldibenzo[b,d]thiophene-2-sulfonate (12)

To a dry round bottom flask under inert atmosphere, phenyl 8-bromodibenzo[b,d]thiophene-2-sulfonate (5, 1.006 g, 0.0024 mol), K$_3$PO$_4$ (1.020 g, 0.0047 mol), Pd(dppf)Cl$_2$ (0.352 g, 0.0004 mol), and octylboronic acid (0.456 g, 0.0029 mol) were combined. 100 mL toluene was added to the flask after it had been degassed by nitrogen bubbling for 15 minutes. The solution was refluxed for 24 hours and then cooled to room temperature. The solution was then poured over 100 mL saturated ammonium chloride (aq). The bilayer was washed with DCM (3×150 mL). The organic washes were collected and concentrated under reduced pressure, producing a dark grey solid. The crude solid was separated by normal phase flash chromatography using hexanes/ethyl acetate (9/1) as the eluent. The column produced a clear oil which crystallized at room temperature, affording the product in 32% yield. (0.345 g, 0.0007 mol). $^1$H NMR (DMSO-$d_6$, 400 MHz): δ (ppm) 8.90 (s, 1H), 8.46 (s, 1H), 8.30 (d, J=8.6 Hz, 1H), 7.99 (d, J=8.3 Hz, 1H), 7.84-7.88 (m, 1H), 7.44 (d, J=8.1 Hz, 1H), 7.32-7.39 (m, 2H), 7.25-7.31 (m, 1H), 7.07 (d, J=8.3 Hz, 2H), 2.74 (t, J=7.7 Hz, 2H), 1.60-1.71 (m, 2H), 1.13-1.37 (m, 10H), 0.82 (t, J=6.6 Hz, 3H) $^{13}$C NMR (DMSO-$d_6$, 151 MHz): δ (ppm) 149.1, 145.6, 140.1, 136.5, 135.4, 134.1, 130.7, 130.1, 129.2, 127.5, 125.2, 124.4, 122.9, 122.5, 122.1, 122.1, 35.0, 31.3, 31.1, 28.8, 28.7, 28.7, 22.1, 13.9 HRMS (FAB) m/z: [M+Na]+ calcd for $C_{26}H_{28}O_3S_2$: 475.137758; found: 475.13776.

phenyl 8-decyldibenzo[b,d]thiophene-2-sulfonate (13)

To a dry round bottom flask under inert atmosphere, phenyl 8-bromodibenzo[b,d]thiophene-2-sulfonate (5, 1.002 g, 0.0024 mol), $K_3PO_4$ (1.021 g, 0.0047 mol), Pd(dppf)Cl$_2$ (0.356 g, 0.0004 mol), and butylboronic acid (0.519 g, 0.0029 mol) were combined. 100 mL toluene was added to the flask after it had been degassed by nitrogen bubbling for 15 minutes. The solution was refluxed for 24 hours and then cooled to room temperature. The solution was then poured over 100 mL saturated ammonium chloride (aq). The bilayer was washed with DCM (3×150 mL). The organic washes were collected and concentrated under reduced pressure, producing a dark grey solid. The crude solid was separated by normal phase flash chromatography using hexanes/ethyl acetate (9/1) as the eluent. The column produced a clear oil which crystallized at room temperature, affording the product in 20% yield. (0.232 g, 0.0005 mol). $^1$H NMR (DMSO-$d_6$, 400 MHz): δ (ppm) 8.91 (d, J=1.7 Hz, 1H), 8.47 (s, 1H), 8.30 (d, J=8.6 Hz, 1H), 8.00 (d, J=8.3 Hz, 1H), 7.86 (dd, J=8.6, 2.0 Hz, 1H), 7.46 (dd, J=8.2, 1.6 Hz, 1H), 7.32-7.39 (m, 2H), 7.25-7.31 (m, 1H), 7.05-7.10 (m, 2H), 2.75 (t, J=7.6 Hz, 2H), 1.62-1.72 (m, 2H), 1.14-1.37 (m, 14H), 0.79-0.85 (m, 3H) $^{13}$C NMR (DMSO-$d_6$, 151 MHz): δ (ppm) 149.1, 145.6, 140.1, 136.6, 135.4, 134.1, 130.7, 130.1, 129.2, 127.5, 125.2, 124.4, 122.9, 122.6, 122.1, 122.1, 35.0, 31.3, 31.1, 29.0, 29.0, 28.8, 28.7, 22.1, 13.9 HRMS (FAB) m/z: [M+Na]+ calcd for $C_{28}H_{32}O_3S_2$: 503.169059; found: 503.16907.

Coupling of secondary alkyl boronic acids to compound 5 was the least efficient coupling. Initially, the coupling of isopropyl boronic and 5 was investigated; however, only a 24% yield was achieved (Table 3, Entry 2). This low yield was complicated by an unidentified byproduct possessing the same m/z as the product. The unidentified byproduct was suspected as the n-propyl analog and could not be separated from the target molecule on a preparative scale.

Scheme 5: Optimized secondary alkyl coupling conditions for cyclopropyl (14)

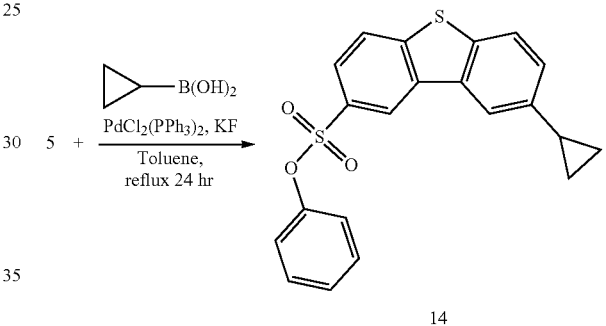

TABLE 3

Coupling of Secondary Alkyl Groups

| Entry | B(OH)$_2$ | Catalyst | Loading (mol %) | Base | Solvent System | Product | Yield |
|---|---|---|---|---|---|---|---|
| 1 | isopropyl | PdCl$_2$(PPh$_3$)$_2$ | 10% | KF | Toluene | — | 0% |
| 2 | isopropyl | Pd(dppf)Cl$_2$ | 20% | K$_3$PO$_4$ | Toluene | — | 24%$^a$ |
| 3 | cyclohexyl | PdCl$_2$(PPh$_3$)$_2$ | 10% | KF | Toluene | — | 0% |
| 4 | cyclohexyl | C$_{24}$H$_{54}$P$_2$Pd$^b$ | 5% | K$_3$PO$_4$ | Toluene | — | 0% |
| 5 | cyclohexyl | C$_{24}$H$_{54}$P$_2$Pd$^b$ | 5% | Na$_2$B$_4$O$_7$ | DME/H$_2$O (50/50) | — | 0% |
| 6 | cyclohexyl | C$_{24}$H$_{54}$P$_2$Pd$^b$ | 5% | Na$_2$B$_4$O$_7$ | Dioxane$^c$ | — | 0% |
| 7 | cyclohexyl | C$_{24}$H$_{54}$P$_2$Pd$^b$ | 5% | KF | Dioxane$^c$ | — | 0% |
| 8 | cyclohexyl | C$_{24}$H$_{54}$P$_2$Pd$^b$ | 5% | KF | Dioxane$^c$ | — | 0% |
| 9 | cyclopentyl | PdCl$_2$(PPh$_3$)$_2$ | 10% | KF | Toluene | — | 0% |
| 10 | cyclopentyl | Pd(dppf)Cl$_2$ | 20% | K$_3$PO$_4$ | Toluene | — | 0% |
| 11 | cyclopropyl | Pd(dppf)Cl$_2$ | 20% | K$_3$PO$_4$ | Toluene | 14 | 25%$^a$ |
| 12 | cyclopropyl | PdCl$_2$(PPh$_3$)$_2$ | 10% | K$_3$PO$_4$ | Toluene | 14 | 66%$^d$ |
| 13 | cyclopropyl | PdCl$_2$(PPh$_3$)$_2$ | 10% | KF | Toluene | 14 | 65%$^e$ |

$^a$Yield based on GCMS.
$^b$Bis(tri-tert butylphosphine)palladium (0).
$^c$Solvent underwent freeze, pump, thaw.
$^d$Yield based on GCMS, contains excessive side product. Reaction ran for 36 hours In addition to isopropyl boronic acid, cycloalkyl boronic acids were investigated. Despite attempting a variety of conditions with cyclohexyl boronic acid and cyclopentyl boronic acid, no coupled product could be obtained (Table 3, Entry 3-10). For cyclopropyl boronic acid two sets of conditions displayed good coupling. The conditions noted in Entry 12 provided a 66% yield; however, the crude product mixture contained unreacted and dehalogenated compound 5 as indicated by GCMS. The presence of unreacted and dehalogenated compound 5 was eliminated by using KF as the base, which produced a 65% yield without any of the byproducts which had previously stalled purification (Table 3, Entry 13).

In summary, a versatile method to couple a variety of hydrocarbon groups to unsymmetrical dibenzothiophenes has been identified. This work provides conditions to couple aromatic, vinylic, primary alkyl and secondary alkyl groups using Suzuki coupling.

Example 2

A series sulfoxide and sulfone analogs of compounds 6, 7, and 8 of Example 1 were prepared according to Scheme 6.

Scheme 6

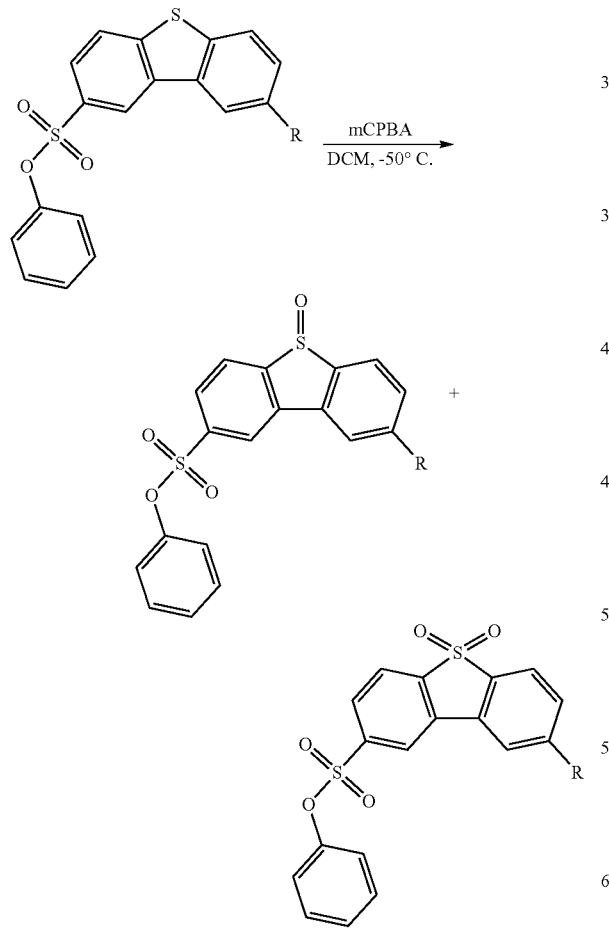

Compounds 6, 7, and 8 (4 mmol) were each dissolved in $CH_2Cl_2$ (1 L), and each solution was cooled to −50° C. Then, mCPBA (5 mmol) was added to each. The reactions were allowed to stir overnight, and then the reaction products were concentrated under vacuum. The resulting solids were purified by silica chromatography using DCM for four column volumes followed by 1% ethyl acetate/99% DCM as the eluent to elute the sulfoxides. This afforded sulfones (10-22%) as a white solid. The eluents containing the sulfoxide were concentrated under vacuum. The solids were recrystallized in ethanol affording pure sulfoxides as a white solid (22-45%).

Reaction of the three compounds 6, 7, and 8 produced two new molecules through this reaction. They are denoted at 6a, 6b, 7a, 7b, 8a or 8b henceforth. In these designations the letter denotes the number of oxygen atoms (i.e., 'a' is sulfoxide and 'b' is sulfone). The analytical results for each compound are provided below phenyl 8-phenyldibenzo[b,d]thiophene-2-sulfonate 5-oxide (6a)

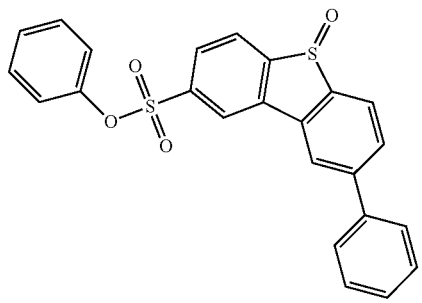

$^1$H NMR (DMSO-$d_6$, 400 MHz): δ (ppm) 9.03 (d, J=1.6 Hz, 1H), 8.85 (d, J=1.5 Hz, 1H), 8.37 (d, J=8.1 Hz, 1H), 8.23 (d, J=8.1 Hz, 1H), 7.99 (ddd, J=8.0, 6.0, 1.7 Hz, 2H), 7.90-7.95 (m, 2H), 7.51-7.59 (m, 2H), 7.45-7.51 (m, 1H), 7.37-7.44 (m, 2H), 7.29-7.37 (m, 1H), 7.12-7.19 (m, 2H) $^{13}$C NMR (DMSO-$d_6$, 101 MHz): δ (ppm) 151.1, 148.9, 144.9, 143.8, 138.6, 138.3, 138.2, 136.0, 130.2, 129.3, 129.0, 128.9, 128.7, 128.2, 127.7, 127.3, 122.8, 122.2, 122.0.

phenyl 8-phenyldibenzo[b,d]thiophene-2-sulfonate 5,5-dioxide (6b)

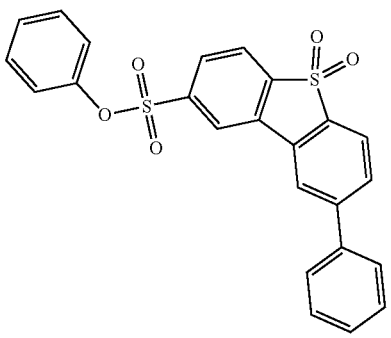

$^1$H NMR (DMSO-$d_6$, 400 MHz): δ (ppm) 9.13 (d, J=1.5 Hz, 1H), 8.91 (d, J=1.2 Hz, 1H), 8.27 (d, J=8.1 Hz, 1H), 8.16 (d, J=8.1 Hz, 1H), 8.05 (td, J=8.1, 1.6 Hz, 2H), 7.91-7.97 (m, 2H), 7.47-7.60 (m, 3H), 7.38-7.46 (m, 2H), 7.31-7.38 (m, 1H), 7.15-7.21 (m, 2H) $^{13}$C NMR (DMSO-$d_6$, 101 MHz): δ

(ppm) 148.9, 146.7, 142.2, 140.2, 137.8, 135.4, 132.9, 130.9, 130.3, 130.2, 130.0, 129.09, 129.07, 127.8, 127.4, 123.4, 123.2, 122.8, 122.4, 122.1.

phenyl 8-(naphthalen-1-yl)dibenzo[b,d]thiophene-2-sulfonate 5-oxide (7a)

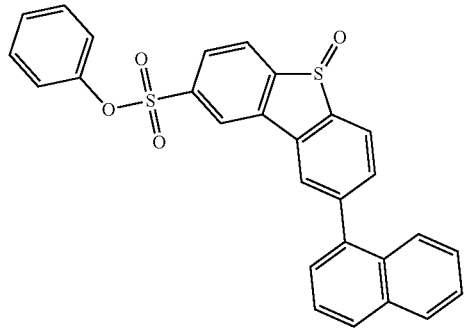

7a $^1$H NMR (DMSO-d$_6$, 400 MHz): δ (ppm) 9.06 (d, J=1.5 Hz, 1H), 8.99 (d, J=1.5 Hz, 1H), 8.51 (s, 1H), 8.38 (d, J=8.1 Hz, 1H), 8.29 (d, J=8.1 Hz, 1H), 8.16 (dd, J=8.2, 1.6 Hz, 1H), 8.05-8.12 (m, 2H), 7.97-8.03 (m, 2H), 7.86-7.92 (m, 1H), 7.57-7.62 (m, 2H), 7.38-7.45 (m, 2H), 7.30-7.36 (m, 1H), 7.13-7.19 (m, 2H) $^{13}$C NMR (DMSO-d$_6$, 101 MHz): δ (ppm) 151.6, 149.4, 145.2, 144.4, 139.1, 138.8, 136.5, 136.0, 133.6, 133.3, 130.7, 129.8, 129.7, 129.2, 129.1, 128.9, 128.7, 128.2, 128.1, 127.3, 127.1, 126.9, 125.6, 123.3, 122.9, 122.6.

phenyl 8-(naphthalen-1-yl)dibenzo[b,d]thiophene-2-sulfonate 5,5-dioxide (7b)

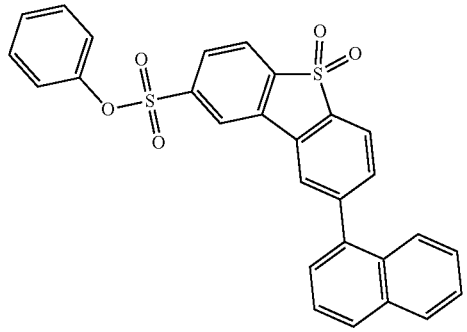

7b $^1$H NMR (DMSO-d$_6$, 400 MHz): δ (ppm) 9.16 (d, J=1.2 Hz, 1H), 9.05 (s, 1H), 8.53 (s, 1H), 8.29 (d, J=8.1 Hz, 1H), 8.18-8.25 (m, 2H), 7.99-8.14 (m, 5H), 7.58-7.65 (m, 2H), 7.39-7.47 (m, 2H), 7.31-7.38 (m, 1H), 7.16-7.21 (m, 2H) $^{13}$C NMR (DMSO-d$_6$, 101 MHz): δ (ppm) 148.9, 146.6, 142.2, 120.2, 135.45, 135.2, 133.1, 133.0, 132.9, 130.9, 130.4, 128.7, 128.5, 127.9, 127.7, 127.0, 126.8, 125.1, 123.5, 123.2, 123.0, 122.6, 122.1.

phenyl 8-([1,1'-biphenyl]-4-yl)dibenzo[b,d]thiophene-2-sulfonate 5-oxide (8a)

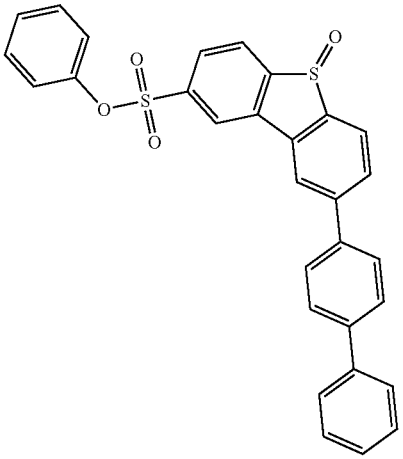

8a $^1$H NMR (DMSO-d$_6$, 400 MHz): δ (ppm) 9.05 (d, J=1.5 Hz, 1H), 8.92 (d, J=1.5 Hz, 1H), 8.37 (d, J=8.1 Hz, 1H), 8.25 (d, J=8.1 Hz, 1H), 7.96-8.09 (m, 4H), 7.85 (d, J=8.4 Hz, 2H), 7.74-7.81 (m, 2H), 7.48-7.55 (m, 2H), 7.38-7.45 (m, 3H), 7.30-7.36 (m, 1H), 7.11-7.19 (m, 2H) $^{13}$C NMR (DMSO-d$_6$, 101 MHz): δ (ppm) 151.1, 148.9, 144.3, 143.9, 140.4, 139.3, 138.6, 138.3, 137.1, 136.1, 130.3, 129.3, 129.0, 128.9, 128.8, 128.7, 128.2, 128.2, 127.8, 127.8, 127.2, 126.7, 125.3, 122.9, 122.1.

phenyl 8-([1,1'-biphenyl]-4-yl)dibenzo[b,d]thiophene-2-sulfonate 5,5-dioxide (8b)

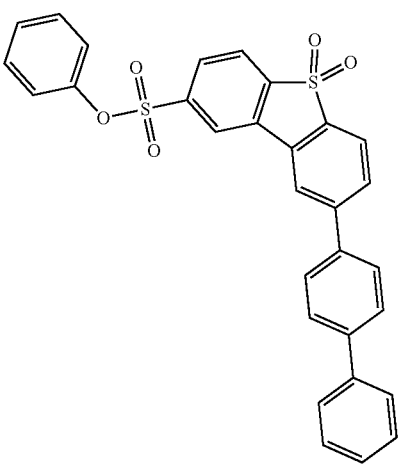

8b $^1$H NMR (DMSO-d$_6$, 400 MHz): δ (ppm) 9.15 (d, J=1.3 Hz, 1H), 8.98 (d, J=1.1 Hz, 1H), 8.28 (d, J=8.1 Hz, 1H), 8.10-8.21 (m, 2H), 8.02-8.09 (m, 3H), 7.87 (d, J=8.6 Hz, 2H), 7.75-7.81 (m, 2H), 7.48-7.56 (m, 2H), 7.39-7.47 (m, 3H), 7.32-7.38 (m, 1H), 7.14-7.22 (m, 2H) $^{13}$C NMR (DMSO-d$_6$, 101 MHz): δ (ppm) 148.9, 146.1, 142.2, 140.8, 140.2, 139.3, 136.7, 135.4, 132.9, 130.9, 130.3, 129.9, 129.1, 128.0, 227.9, 127.3, 125.8, 123.4, 123.2, 123.0, 122.2, 122.1.

Example 3: Excitation and Emission Spectral Analysis of Compounds 6b-8b

General Procedure for Emission and Excitation Data Collection:

Emission:

All data were collected on a SHIMAZDU Spectrofluorometer RF-5301PC. Solutions of the respective compounds were prepared in acetonitrile at approximately 1 mM concentration. Solutions (4 mL) were added to a freshly washed quartz cuvette for measurements. The excitation wavelength was varied between 270 nm and 390 nm in 20 nm intervals until the greatest intensity emission was detected. The emission spectra ranges started at 20 nm to the red of the chosen excitation wavelength up to 780 nm. Scan speed was set at "Very Fast" with both the slit widths set to 1.5 mm.

Excitation:

All data were collected on a SHIMAZDU Spectrofluorometer RF-5301PC. Solutions of the respective compounds were prepared in acetonitrile at approximately 1 mM concentration. Solutions (4 mL) were added to a freshly washed quartz cuvette for measurements. The monitored emission wavelength was set using the high intensity emission from the respective molecule. The scanning range was from 220 nm through 770 nm. Scan speed was set at "Very Fast" with both the slit widths set to 1.5 mm.

Compounds 6b, 8a, 8b, 7b and 7a all luminesced in either a deep blue or near blue wavelength. 6b was excited at 344 nm and emitted at about 437 nm. 7b was excited at 367 nm and emitted at 499 nm. 8a was excited at 365 nm and emitted at 477 nm. 8b was excited at 366 nm and emitted at 475 nm. 6b had a quantum yield of 0.05. FIGS. 1-8 present graphs of the emission and excitation scans of these compounds. FIGS. 9-12 present UV absorbance graphs for these compounds.

Example 4

Compounds 15b, 16b and 17b were synthesized from compounds 6b, 7b, and 8b produced as described in Example 2 using the following scheme.

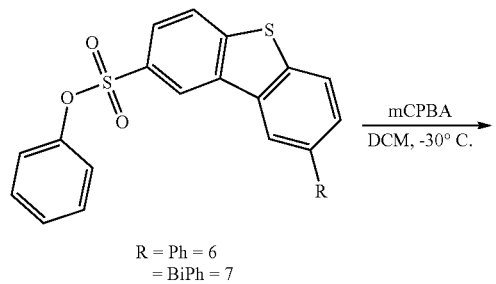

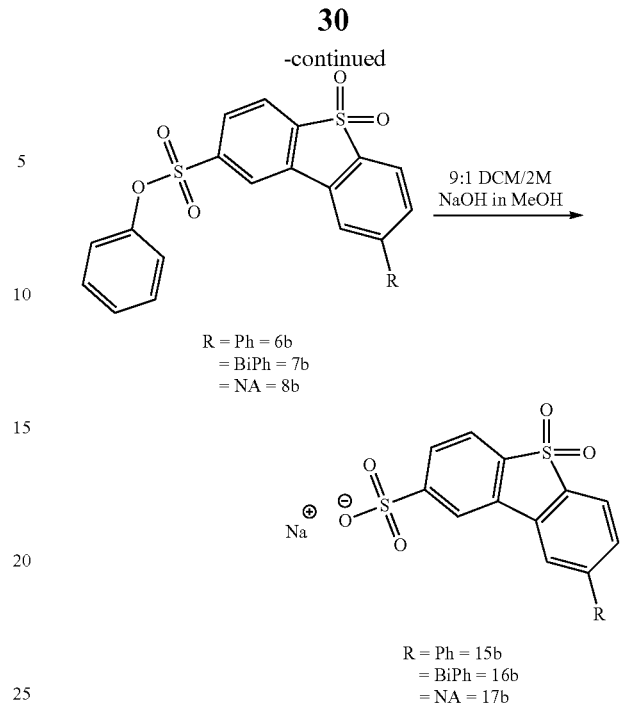

Sulfones 6b, 7b, and 8b, described above, were dissolved in DCM. 2M sodium hydroxide (NaOH) in methanol (MeOH) was added to the solution. The solution was stirred overnight and evaporated under reduced pressure in the presence of reverse phase silica gel. The resulting solid was purified on a preparative reverse phase column using 95% 0.1% TFA water/5% ACN.

sodium 8-phenyldibenzo[b,d]thiophene-2-sulfonate 5,5-dioxide (15b)

$^1$H NMR (DMSO-$d_6$, 400 MHz): δ (ppm) 8.67 (d, J=1.2 Hz, 1H), 8.57 (d, J=0.9 Hz, 1H), 8.01-8.06 (m, 1H), 7.91-7.99 (m, 4H), 7.84-7.89 (m, 1H), 7.51-7.57 (m, 2H), 7.43-7.51 (m, 1H); $^{13}$C NMR (DMSO-$d_6$, 101 MHz): δ (ppm) 154.4, 146.3, 138.1, 137.2, 135.9, 131.7, 130.9, 129.0, 128.8, 128.1, 126.4, 122.4, 121.6, 121.3, 120.3.

sodium 8-([1,1'-biphenyl]-4-yl)dibenzo[b,d]thiophene-2-sulfonate 5,5-dioxide (16b)

$^1$H NMR (DMSO-$d_6$, 400 MHz): δ (ppm) 8.75 (s, 1H), 8.60 (s, 1H), 7.99-8.12 (m, 5H), 7.92-7.98 (m, 1H), 7.81-7.91 (m, 4H), 7.78 (d, J=7.2 Hz, 2H), 7.51 (t, J=7.6 Hz, 3H), 7.41 (s, 1H); $^{13}$C NMR (DMSO-$d_6$, 101 MHz): δ (ppm) 140.5, 139.3, 137.2, 137.0, 135.9, 131.7, 130.9, 129.0, 128.9, 128.2, 128.0, 127.8, 127.2, 126.7, 122.4, 121.6, 121.1, 120.3.

sodium 8-(naphthalen-1-yl)dibenzo[b,d]thiophene-2-sulfonate 5,5-dioxide (17b)

$^1$H NMR (DMSO-$d_6$, 400 MHz): δ (ppm) 8.83 (s, 1H), 8.62 (s, 1H), 8.57 (s, 1H), 8.04-8.15 (m, 6H), 7.94-7.98 (m, 1H), 7.87-7.92 (m, 1H), 7.56-7.64 (m, 2H); $^{13}$C NMR (DMSO-$d_6$, 101 MHz): δ (ppm) 154.4, 146.1, 137.3, 136.0, 135.3, 133.2, 132.9, 131.7, 131.0, 129.3, 128.6, 128.5, 128.2, 127.5, 126.8, 126.7, 126.6, 125.1, 122.5, 121.7, 121.4, 120.3.

Example 5: Photophysical Analysis of Compounds 6b to 8b and 15b to 17b

Excitation/emission data for compounds 6b, 7b, 8b, 15b, 16b, and 17b were collected using the methods described in Example 3 but using a lower concentration of acetonitrile (10 μM). Compounds 15b, 16b and 17b and their parent molecules (6b, 7b and 8b) all luminesce in the visible range and their optical properties are described in Table 4. All the listed compounds' $\lambda_{max}$ absorption ranged between 238-250 nm, which did not correlate to the wavelength of excitation that produced the most intense luminescence ($\lambda_{ex}$). This indicated that the absorption at wavelengths near $\lambda_{max}$ excites the molecules to excited-states above S1 that have non radiative deactivation pathways. The wavelength of $\lambda_{ex}$ for the excitation scan corresponds to excitation to S1, which leads to emission. This $\lambda_{ex}$ for all the molecules were red shifted, or shifted to the direction of longer wavelengths, from the peak absorption by an average 40 nm.

TABLE 4

Photophysical data of Compounds 6b-8b and 15b-17b

| Compound | $\lambda_{abs}$ (nm)[a] | log $\varepsilon_{max}$ (M$^{-1}$ cm$^{-1}$)[d,g] | $\lambda_{ex}$ (nm)[a,b] | $\lambda_{ex}$ (nm)[a,g] | $\lambda_{em}$ (nm)[a] | $\lambda_{em}$ (nm)[g] | Stokes Shift (nm)[c,a] | log $\varepsilon_{ex}$ (M$^{-1}$ cm$^{-1}$)[e] | $\varphi^f$ |
|---|---|---|---|---|---|---|---|---|---|
| 6b | 238 | 4.69 | 274 | 275 | 426 | 434 | 152 | 4.45 | 0.05 |
| 8b | 243 | 4.59 | 283 | 286 | 485 | 478 | 202 | 4.17 | 0.59 |
| 7b | 243 | 4.79 | 274 | 274 | 492 | 486 | 218 | 4.51 | 0.15 |
| 15b | 248 | 4.67 | 268 | 274 | 371 | 380 | 103 | 4.4 | 0.07 |
| 16b | 246 | 4.75[a] | 287 | 284 | 412 | 422 | 125 | 2.48[a] | 0.29 |
| 17b | 250 | 4.67 | 274 | 274 | 421 | 428 | 147 | 4.36 | 0.55 |

[a]Measured in acetonitrile at 10 μM
[b]Excitation wavelength
[c]Calculated from excitation wavelength
[d]Maximum molar extinction coefficient
[e]Molar extinction coefficient at excitation wavelength
[f]Measured using the single-point method in EtOH
[g]Measured in EtOH at 10 μM It was noted that the larger chromophore the more the emission spectra shifts further to the red. The phenyl sulfonate compounds (6b, 7b, and 8b) have a $\lambda_{max}$ of emission ranges from 426-494 nm while the sulfonic acid salt analogs (15b, 16b, and 17b) have $\lambda_{max}$ values between 371-428 nm. The transformation of the sulfonate ester to acid shifts the luminescent emission towards the UV and also reduces the Stokes shift. This transformation does not consistently alter the quantum yield ($\varphi$). The quantum yields were determined using a single point method described in the art (J. R Lakowicz, Principles of Fluorescence Spectroscopy, Springer US 2007). The phenyl analogs (6b and 15b) maintain a low quantum yield, 0.05 and 0.07 respectively, independent of the phenyl sulfonate ester. In the case of the biphenyl analogs, the phenyl sulfonate ester analog (8b) has a quantum yield of 0.59 while the sulfonic acid analog (16b) has a quantum yield of 0.29. The reduction of quantum yield seen with the transformation of the phenyl sulfonate ester to the sulfonic acid salt with regards to 6b and 15b is not seen with 7b and 17b as the phenomenon is inverted. The naphthyl analogs display a higher quantum yield 0.55 when it is a sulfonic acid and a lower quantum yield of 0.15 when it is a phenyl sulfonate ester.

Example 6: Use of Dibenzothiophene Compounds as Cellular Imaging Agents

Preparation of Cells for Confocal Microscopy Studies

Sterile glass cover slips, pre-incubated with culture medium, were placed in sterile 6-well plates. Single cell suspension of the MDA-MB-231 breast carcinoma cell line was prepared at $5 \times 10^4$ cells ml$^{-1}$ in the appropriate medium. Volumes of 2 mL were pipetted into each of the wells containing the coverslips. The 6-well plate was left overnight at 37° C. in a 5% $CO_2$ incubator. Following the overnight incubation, the plate was aspirated dry and then fresh culture medium, containing Compound 16b (at 1 μM and 0.1% DMSO) in a volume of 2 mL, was gently pipetted onto the cell monolayers attached to the glass cover slips. Cells on the cover slips were exposed to Compound 16b for approximately 3 hours. Cells were washed with a 50:1 mixture of HBSS and HEPES. Glass cover slips were removed and mounted on the slides with HBSS/HEPES mixture. The specimen was sealed with clear nail polish before visualized under a microscope.

Confocal Microscopy Imaging

Figure 13:
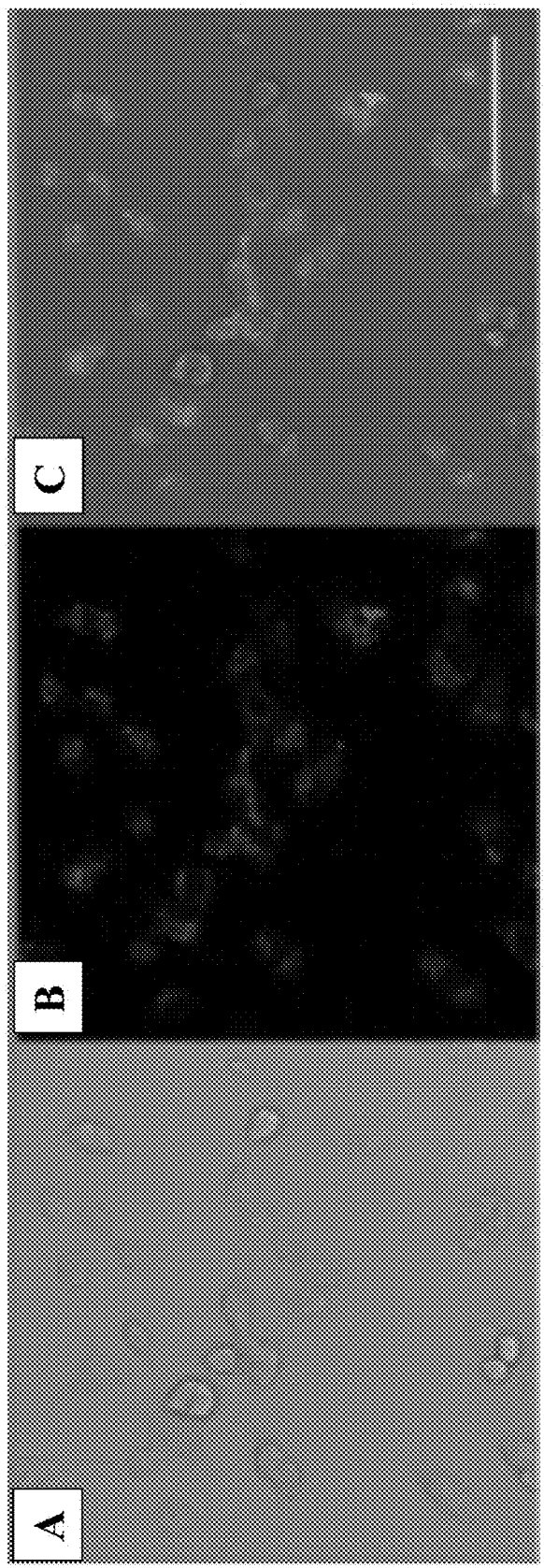
FIG. 13 presents images of a cell line (MDA-MB-231 breast carcinoma) treated with Compound 16b. Panel A is a phase contrast image. Panel B is a fluorescent image. Panel C is a merged image of Panels A and B. The scale bar represents 100 μm.

For this study, horizontal optical sections were collected on a Leica SP8 TCS STED 3× microscope. Slides were configured with a 100× oil immersion lens to capture the datasets. The excitation wavelength was 405 nm and the emission wavelength was 488 nm. FIG. 13 depicts representative images of MDA-MB-231 breast carcinoma cells incubated with Compound 16b (1 μM) for 120 min. Panel A depicts the phase contrast image. Panel B depicts the fluorescent probe image. Panel C depicts the overlay of panel A and B. Each scale bar is 100 μm.

Example 7: Use of Dibenzothiophene Compounds as Imaging Agents in HeLa Cells Cell Cultures and Treatment.

HeLa human cervical carcinoma cell line was obtained from ATCC (Manassas, Va.). The cells were cultured in a humidified incubator at 5% $CO_2$ and 37° C. The cell line was grown in D-MEM (Invitrogen) high glucose supplemented with 10.0% fetal bovine serum (Invitrogen, Carlsbad, Calif.) and 1.0% Penicillin/Streptomycin (Invitrogen, Carlsbad, Calif.) for an environment suitable for cell growth. The culture was sub-cultured every three days to maintain normal cell growth.

Sterile glass PDL coated #1.5 cover slips (NeuVitro), pre-incubated with culture medium, were placed in sterile 6-well plates. Single cell suspension of the HeLa (cervical cancer cells taken from patient Henrietta Lacks) cell line was prepared at $5\times10^4$ cells $ml^{-1}$ in the appropriate medium. Volumes of 2.0 mL were pipetted into each of the wells containing the coverslips. The 6-well plate was left overnight at 37.0° C. in a 5.0% CO2 incubator. Following the overnight incubation, the plate was aspirated dry and then fresh culture medium, containing the drug (at 1.0 µM and 0.10% DMSO) in a volume of 2.0 mL, was gently pipetted onto the cell monolayers attached to the glass cover slips. Cells on the cover slips were exposed to the drug for approximately 2 hours. Cells were washed with PBS and treated with 4.0% paraformaldehyde solution prepared in PBS, incubated for 30 minutes at room temperature for full permeabilization. Several washes with PBS were completed to ensure excess solution was rinsed away. Glass cover slips were removed and mounted on slides with ProLong Gold Antifade Mountant (ThermoFisher Scientific). The specimen was dried for several minutes and sealed with clear nail polish before visualized under a microscope Cell Image Captures: All images were captured with a Leica DM 4000 B microscope with a DFC3000G camera (Leica Microsystems, Germany) and 63× oil immersion lens. HeLa cells were staged according to the method above. Leica LASX Core Software (Leica Microsystems, Germany) was used to acquire the images.

Figure 14:
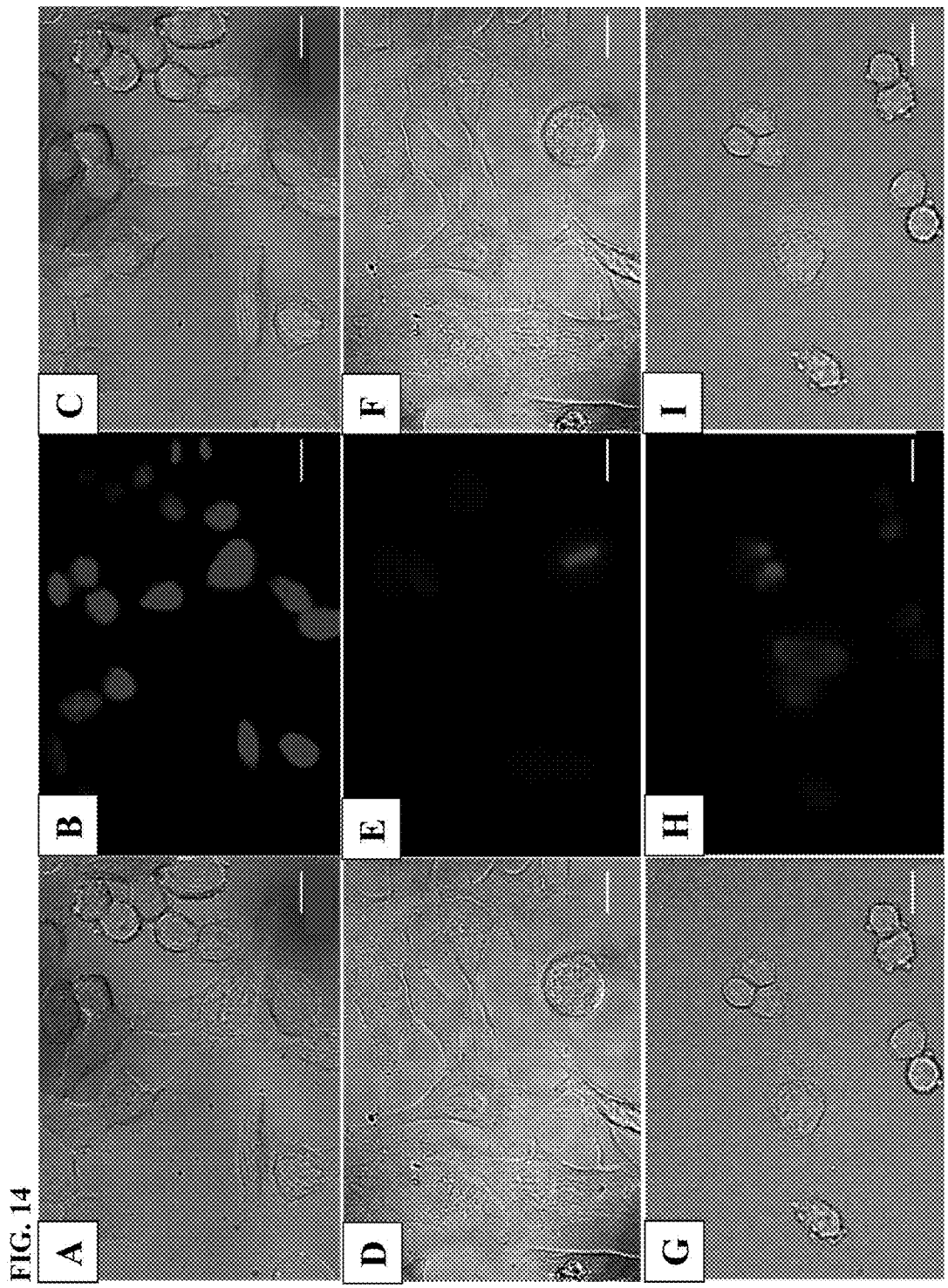
FIG. 14 presents images of a cell line (HeLa cervical cancer) treated with Compounds 16b, 15b, and 17b. Panels A, D, G are phase contrast images of cells treated with Compounds 16b, 15b, and 17b respectively. Panels B, E, H are fluorescent images of the same cells, respectively. Panels C, F, and I are merged images of Panels A, D, G with Panels B, E, H, respectively. The scale bars in each panel represent 50 μm.

Stained cells were clearly observed by exciting the cells with a broadly emitting lamp using DAPI filter set. Luminescence was observed within the cell bodies of the HeLa cells upon excitation of the UV wavelengths. The excitation wavelength was 350 nm and the emission wavelength was approximately 400 nm. FIG. 14 depicts representative images of HeLa cervical cancer cell lines incubated with Compounds 16b, 15b, and 17b (1 µM) for 120 min. Bright field images of cells incubated with compounds 16b, 15b, and 17b are shown in Panels A, D, and G, respectively. Luminescence from each compound (16b, 15b, and 17b) is shown in Panels B, E, and H, respectively, with UV laser radiation. Compounds 16b and 15b showed intense luminescence while only slight luminescence is seen with Compound 17b. When the bright field images of the cells are merged with UV observed compounds, luminescence is clearly identified within the nucleus of the cell for Compounds 16b, 15b, and 17b (Panels C, E, and I, respectively).

FIG. 14 also provides evidence that Compounds 16b and 15b track with chromosomes during mitosis. Panels A-C (Compound 16b) and Panels D-F (Compound 15b) show at least one cell undergoing mitosis (upper right corner of panels A-C and bottom right of D-F). For 16b (Panel B and C), the luminescence reveals that the cells are in anaphase or telophase. Luminescence for Compound 15b (Panels D and F) forms a pillar shape indicating the chromosomes are lining up at the metaphase plate.

Example 8: Compounds Show Little Cell Toxicity

To determine whether long-term exposure to each compound could be toxic to cells, Hela cells were treated with varying concentrations of Compounds 16b, 15b and 17b for 72 hours. An anti-proliferation protocol was carried out by testing chosen compounds on the growth of the human cervical cancer cell lines. HeLa cells were cultured in their respective media supplemented with 10.0% FBS (fetal bovine serum) and 1.0% Pen/Strep. Cells (1,000 cells/100 µL per well) were plated in a 96-well culture plate (TC treated, Greiner) and incubated for 24 h. 50 µL (DMSO <1%) of the compound at final concentrations 100 µM, 10 µM, 1 µM, 100 nM, 10 nM, and 1 nM were added to the appropriate wells. Triplicates wells were performed for each compound, on three identical plates.

After incubation of the cells, at 37° C. in a humidified atmosphere of 5% CO2 for 72 hours, the cells were stained and incubated with MTS (3-(4,5-dimethylthiazol-2-yl)-5-(3-carboxymethoxyphenyl)-2-(4-sulfophenyl)-2H-tetrazolium) reagent in the presence of PMS (phenazine methosulfate) reagent for 2 hours to determine cell viability. An MTS assay is based on the reduction of the MTS tetrazolium compound by viable cells to generate a colored formazan dye that is soluble in cell culture media. The absorbance of each well was taken at 490 nm using a multimode plate reader (FlexStation 3, Molecular Devices, San Diego, Calif.). GraphPad Prism was used to analyze transposed data to determine the percent viability. A two-way ANOVA was used to determine if the means of the compounds are significantly different from each other. Each compound was tested in at least triplicate.

Figure 15:
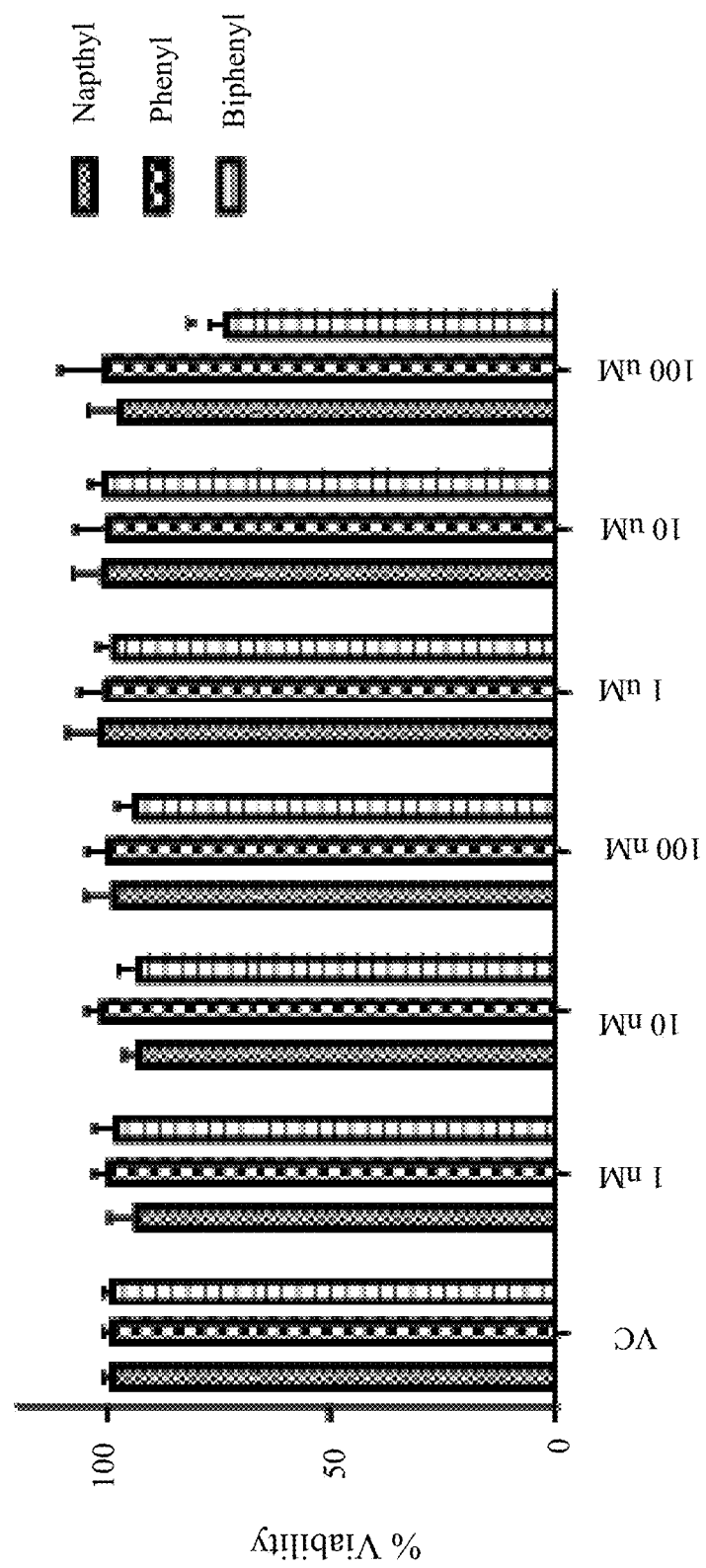
FIG. 15 is a bar graph depicting the results of an antiproliferation assay showing the cytotoxicity of HeLa cells after 72 h treated with dibenzothiophene-S-dioxide compound derivatives along with controls. Compounds are identified by their functional group (Biphenyl (16b), Phenyl (15b), or Napthyl (17b)). The symbol (*) denotes a P<0.05 in comparison to the vehicle control and other treated cells (the example of statistical significance in comparison to the other treated and untreated control cells using a two-way ANOVA (P<0.05) by Tukey's mean comparison

The percentage of viable cells after each treatment is depicted in FIG. 15. In the figure, each treatment is identified by the functional group attached to the sulfone backbone (e.g., biphenyl (Compound 16b), phenyl (Compound 15b), or napthyl (Compound 17b). The $IC_{50}$ for all of the compounds is in excess of 100 µM as seen in FIG. 15. The biphenyl analog (Compound 16b) begins to show some degree of toxicity at 100 µM; however, the others (Compounds 15b and 17b) do not show any decrease in cell viability at any concentration tested. Interestingly, while Compound 17b seemed to influence the morphology of HeLa cells (FIG. 14, panel G), there was no observed cytotoxicity. Overall, Compounds 15b and 16b are promising nuclear stains with low cytotoxicity.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions, products, and processes without departing from the scope of the invention, it is intended that all matter contained in the above description shall be interpreted as illustrative and not in a limiting sense.

Having described the invention in detail, it will be apparent that modifications and variations are possible without departing from the scope of the invention defined in the appended claims.

REFERENCES

1. Grimsdale, A. C.; Leok Chan, K.; Martin, R. E.; Jokisz, P. G.; Holmes, A. B. *Chemical Reviews* 2009, 109, 897-1091.
2. Nag, M.; Jenks, W. S. *The Journal of Organic Chemistry* 2004, 69, 8177-8182.
3. WAUCHOPE, O. R.; SHAKYA, S.; SAWWAN, N.; LIEBMAN, J. F.; GREER, A. *Journal of Sulfur Chemistry* 2007, 28, 7.
4. Korang, J.; Emahi, I.; Grither, W. R.; Baumann, S. M.; Baum, D. A.; McCulla, R. D. *RSC Advances* 2013, 3, 12390-12397.

5. Bourdillon, M. T.; Ford, B. A.; Knulty, A. T.; Gray, C. N.; Zhang, M.; Ford, D. A.; McCulla, R. D. *Photochemistry and Photobiology* 2014, 90, 386-393.
6. Miller, S. C. *The Journal of Organic Chemistry* 2010, 75, 4632-4635.
7. Na, Y.-J.; Song, W.; Lee, J. Y.; Hwang, S.-H. *Dalton Transactions* 2015, 44, 8360-8363.
8. Cai, X.; Padmaperuma, A. B.; Sapochak, L. S.; Vecchi, P. A.; Burrows, P. E. *Applied Physics Letters* 2008, 92, 083308.
9. Na, Y. J.; Song, W.; Lee, J. Y.; Hwang, S. H. *Organic Electronics: physics, materials, applications* 2015, 22, 92-97.
10. Pahlavanlu, P.; Christensen, P. R.; Therrien, J. A.; Wolf, M. O. *The Journal of Physical Chemistry C* 2016, 120, 70-77.
11. Barder, T. E.; Walker, S. D.; Martinelli, J. R.; Buchwald, S. L. *Journal of the American Chemical Society* 2005, 127, 4685-4696.
12. Tlach, B. C.; Tomlinson, A. L.; Bhuwalka, A.; Jeffries-El, M. *The Journal of Organic Chemistry* 2011, 76, 8670-8681.

What is claimed is:

1. A compound having the structure of Formula (I) or Formula (II) or a salt thereof:

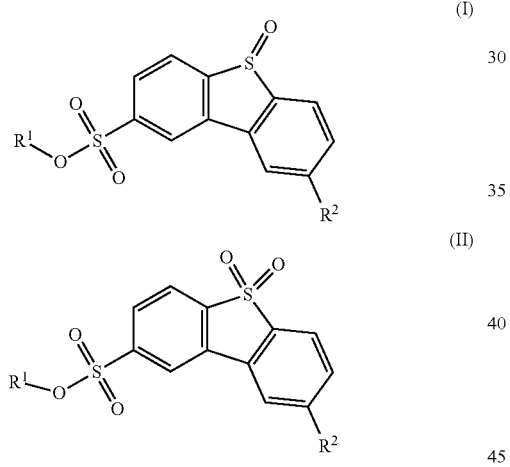

wherein each $R^1$ is independently hydrogen, substituted or unsubstituted aryl or substituted or unsubstituted heteroaryl; and each $R^2$ is independently substituted or unsubstituted aryl or substituted or unsubstituted heteroaryl.

2. The compound of claim 1, wherein the substituted aryl and the substituted heteroaryl are substituted by one or more substituents selected from the group consisting of hydroxy, oxo, halo, amino, substituted or unsubstituted $C_1$-$C_{20}$ alkyl, substituted or unsubstituted $C_1$-$C_{20}$ alkoxy, $C_1$-$C_{20}$ haloalkyl, $C_1$-$C_{20}$ haloalkoxy, and combinations thereof.

3. The compound of claim 1, wherein the substituted or unsubstituted heteroaryl is a substituted or unsubstituted nitrogen-containing heteroaryl.

4. The compound of claim 1, wherein each $R^1$ is independently hydrogen, substituted or unsubstituted phenyl, substituted or unsubstituted biphenyl, substituted or unsubstituted naphthyl, or substituted or unsubstituted anthracenyl and each $R^1$ is independently substituted or unsubstituted phenyl, substituted or unsubstituted biphenyl, substituted or unsubstituted naphthyl, or substituted or unsubstituted anthracenyl.

5. The compound of claim 1, wherein each $R^1$ is independently hydrogen, phenyl, hydroxyphenyl, ethylphenyl, carboxyphenyl, naphthyl, anthracenyl, biphenyl, tolyl, cumyl, styryl, ortho-xylyl, meta-xylyl, para-xylyl, fluorophenyl, chlorophenyl, bromobenzyl, or iodobenzyl and each $R^2$ is independently phenyl, hydroxyphenyl, ethylphenyl, carboxyphenyl, naphthyl, anthracenyl, biphenyl, tolyl, cumyl, styryl, ortho-xylyl, meta-xylyl, para-xylyl, fluorophenyl, chlorophenyl, bromobenzyl, or iodobenzyl.

6. The compound of claim 1, wherein each $R^1$ is independently hydrogen, phenyl, biphenyl, or naphthyl.

7. The compound of claim 1, wherein the compound is selected from the group consisting of:

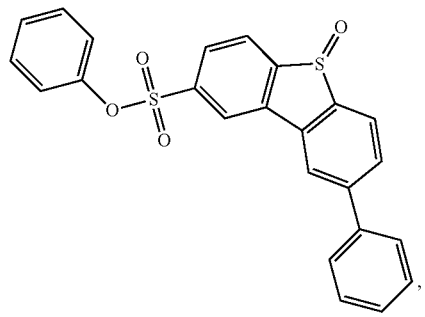

,

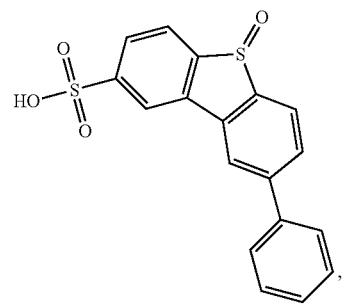

,

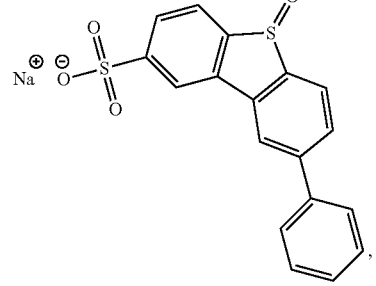

,

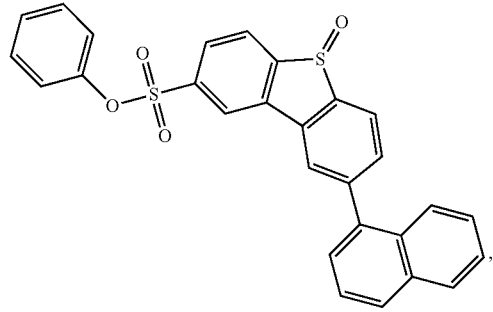

,

-continued
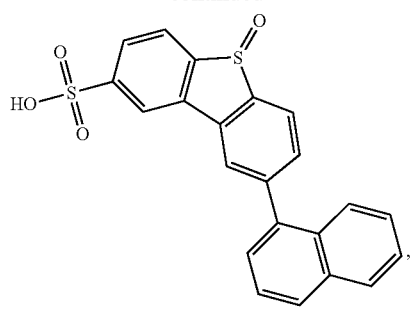
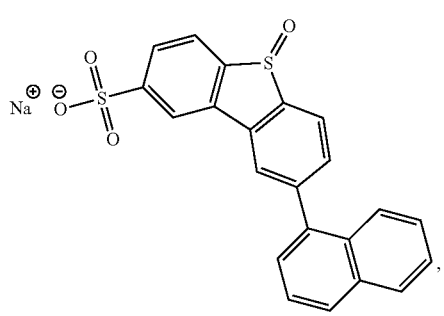
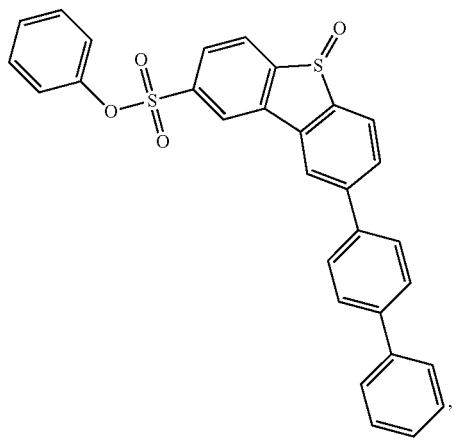
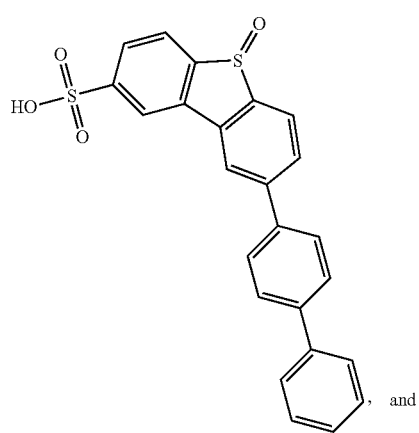, and
-continued
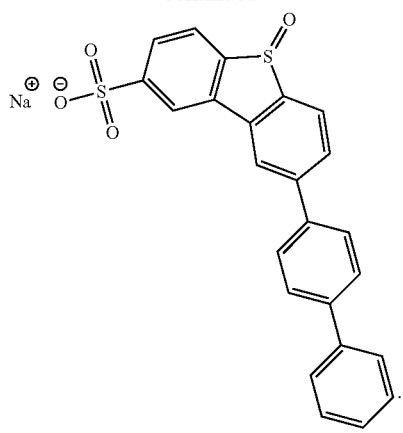
8. The compound of claim 1, wherein the compound is selected from the group consisting of:
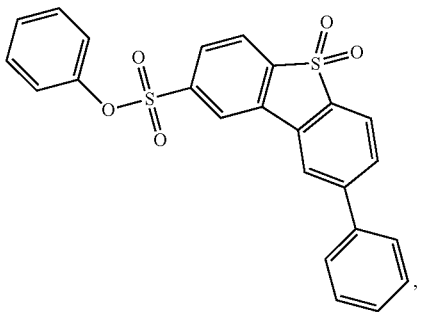
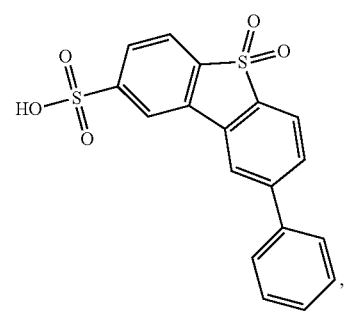
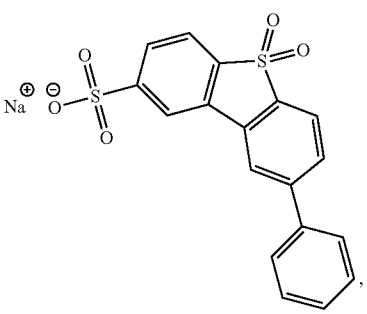,

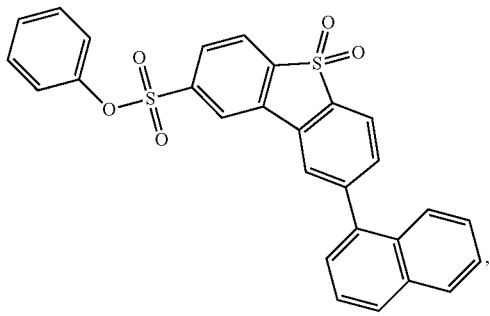
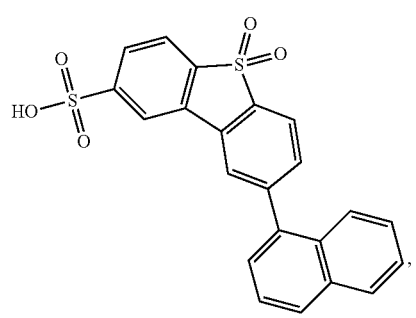
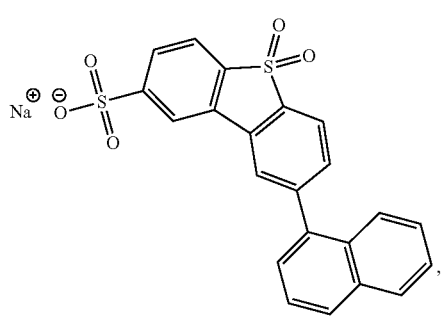
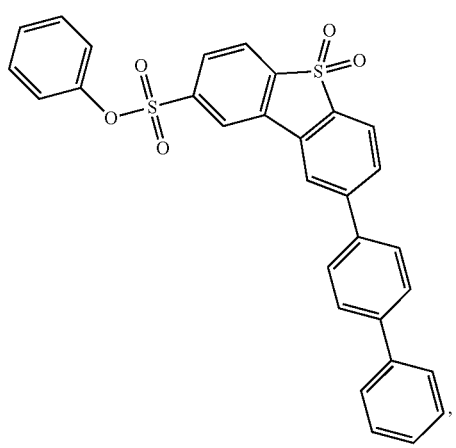
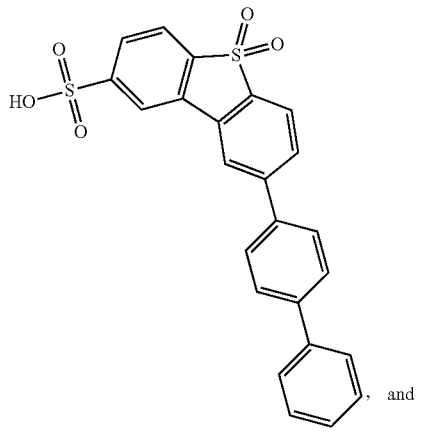
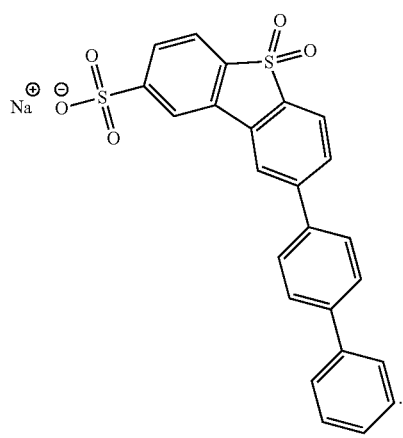
9. A process for preparing a compound of Formula (I) or Formula (II):
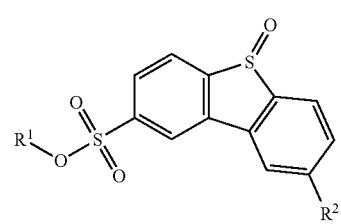
(I)
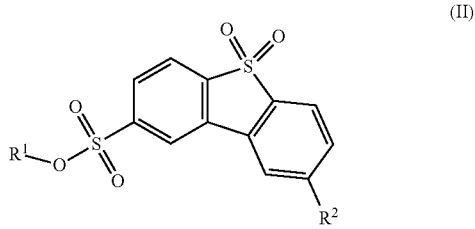
(II)
the process comprising reacting a compound having the structure of Formula (III) with a peroxy acid in the presence of a solvent to form the compound of Formulas (I) and/or (II), wherein Formula (III) has the structure:

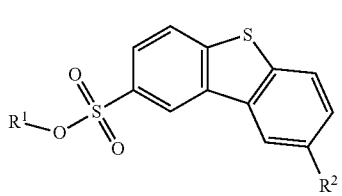

(III)

wherein each $R^1$ is independently substituted or unsubstituted aryl or substituted or unsubstituted heteroaryl; and each $R^2$ is independently substituted or unsubstituted aryl or substituted or unsubstituted heteroaryl.

10. The process of claim 9, wherein the process further comprises reacting a compound of Formula (IV):

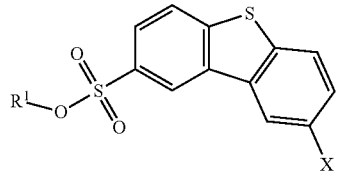

(IV)

with a boronic acid in the presence of a catalyst comprising a transition metal and a solvent under basic conditions to produce the compound of Formula (III), wherein $R^1$ is independently substituted or unsubstituted aryl or substituted or unsubstituted heteroaryl; and X is halogen.

11. The process of claim 10, further comprising reacting a compound of Formula (V):

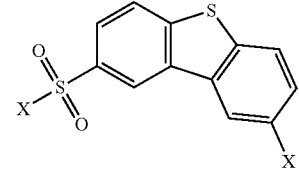

(V)

with a substituted or unsubstituted aryl alcohol or substituted or unsubstituted heteroaryl alcohol in the presence of a bicyclic amine catalyst comprising 1,4-diazabicyclo[2.2.2]octane to produce the compound of Formula (IV), wherein, in Formula (V), each X is independently a halogen.

12. The process of claim 11, further comprising reacting a compound of Formula (VI):

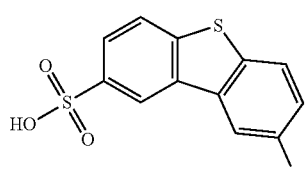

(VI)

with a thionyl halide in the presence of a solvent to produce the compound of Formula (V), wherein, in Formula (VI), X is halogen.

13. The process of claim 12, further comprising reacting a compound of structure Formula (VII):

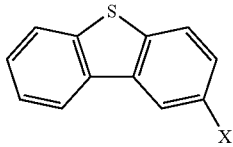

(VII)

with a sulfonic acid source in the presence of a solvent to produce the compound of Formula (VI), wherein, in Formula (VII), X is halogen.

14. The process of claim 13, further comprising reacting a compound of Formula (VIII):

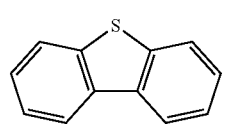

(VIII)

with a halogen source in the presence of a solvent to produce a compound of Formula (VII).

15. A process for preparing a compound of Formula (IX) or (X), or a salt thereof:

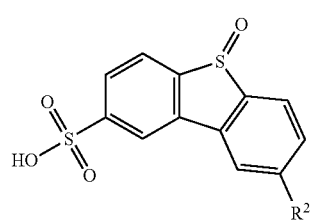

(IX)

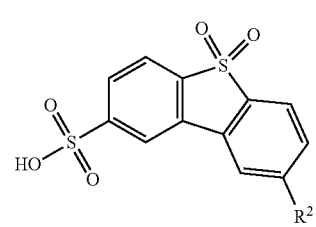

(X)

the process comprising reacting a compound of Formula (I) or Formula (II) with an amount of NaOH in the presence of a solvent to form the compound of Formula (IX) or (X), wherein Formula (I) and Formula (II) have the structure:

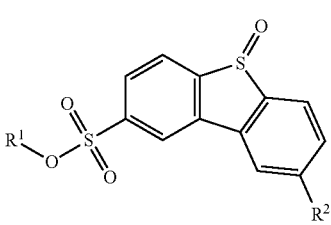

(I)

-continued

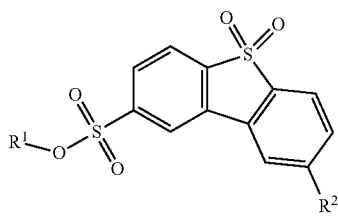

(II)

wherein each $R^1$ is independently substituted or unsubstituted aryl or substituted or unsubstituted heteroaryl; and each $R^2$ is independently substituted or unsubstituted aryl or substituted or unsubstituted heteroaryl.

16. An organic light-emitting diode (OLED) comprising:
a first electrode;
a second electrode; and
an emissive layer positioned between the first electrode and the second electrode,
wherein the emissive layer comprises one or more compounds of claim 1.

17. A display comprising the organic light-emitting diode of claim 16.

18. A process for preparing an organic light-emitting diode comprising:
forming a first electrode on a substrate;
forming an emissive layer comprising one or more compounds of claim 1; and
forming a second electrode;
wherein the emissive layer is positioned between the first electrode and the second electrode.

19. An imaging agent comprising one or more of the compounds of claim 1.

20. A process of visualizing a cell comprising applying the imaging agent of claim 19 to the cell, applying light to stimulate the emission of a luminescent signal from the imaging agent, and detecting the signal.

21. The compound of claim 1 wherein each $R^2$ is independently phenyl, biphenyl, or naphthyl.

22. The compound of claim 1 wherein the compound has the structure of Formula (II) or a salt thereof.

23. The process of claim 19 wherein the imaging agent comprises a compound of Formula II.

24. An imaging agent comprising the compound of claim 22.

25. A process of visualizing a cell comprising applying the imaging agent of claim 24 to the cell, applying light to stimulate the emission of a luminescent signal from the imaging agent, and detecting the signal.

* * * * *

UNITED STATES PATENT AND TRADEMARK OFFICE
CERTIFICATE OF CORRECTION

PATENT NO. : 10,221,153 B2  
APPLICATION NO. : 15/970584  
DATED : March 5, 2019  
INVENTOR(S) : John T. Petroff, II, Ryan D. McCulla and Christopher Arnatt Page 1 of 1

It is certified that error appears in the above-identified patent and that said Letters Patent is hereby corrected as shown below:

In the Claims

Claim 4, Column 35, Line 64:
"and each $R^1$ is independently substituted or unsubstituted"
Should read:
-- and each $R^2$ is independently substituted or unsubstituted --.

Claim 23, Column 44, Line 17:
"23. The process of claim 19 wherein the imaging agent"
Should read:
-- 23. The process of claim 20 wherein the imaging agent --.

Signed and Sealed this  
Twentieth Day of August, 2019

Andrei Iancu  
*Director of the United States Patent and Trademark Office*